US008314265B2

(12) United States Patent
Shukla et al.

(10) Patent No.: US 8,314,265 B2
(45) Date of Patent: Nov. 20, 2012

(54) AROMATIC AMIC ACIDS OR AMIC ESTERS AND COMPOSITIONS

(75) Inventors: Deepak Shukla, Webster, NY (US); Dianne M. Meyer, Hilton, NY (US); Wendy G. Ahearn, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 153 days.

(21) Appl. No.: 12/770,803

(22) Filed: Apr. 30, 2010

(65) Prior Publication Data

US 2011/0269967 A1 Nov. 3, 2011

(51) Int. Cl.
*C07C 229/34* (2006.01)

(52) U.S. Cl. .......................................... 560/37; 562/442

(58) Field of Classification Search .................. None
See application file for complete search history.

(56) References Cited

U.S. PATENT DOCUMENTS

| | | | |
|---|---|---|---|
| 3,533,798 A | 10/1970 | Muller et al. | |
| 4,496,731 A | 1/1985 | Spietschka et al. | |
| 4,831,140 A * | 5/1989 | Spietschka et al. | 546/37 |
| 6,963,080 B2 | 11/2005 | Afzali-Ardakani et al. | |
| 7,198,977 B2 | 4/2007 | Shukla et al. | |
| 7,326,956 B2 | 2/2008 | Shukla et al. | |
| 7,422,777 B2 | 9/2008 | Shukla et al. | |
| 7,572,939 B2 | 8/2009 | Chow et al. | |
| 7,579,619 B2 | 8/2009 | Shukla et al. | |
| 7,629,605 B2 | 12/2009 | Shukla et al. | |
| 7,649,199 B2 | 1/2010 | Shukla et al. | |
| 2002/0164835 A1 | 11/2002 | Dimitrakopoulos et al. | |
| 2005/0176970 A1 | 8/2005 | Marks et al. | |
| 2008/0135833 A1 | 6/2008 | Shukla et al. | |
| 2009/0256137 A1 | 10/2009 | Shukla et al. | |

FOREIGN PATENT DOCUMENTS

WO 2009/126203 10/2009

OTHER PUBLICATIONS

John A. Kreuz et al, "Studies of Thermal Cyclizations of Polyamic Acids and Tertiary Amine Salts", J. of Polymer Sci.: Part A-1, vol. 4, 2607-2616 (1966).
C. Genies et al, "Soluble sulfonated naphthalenic polyimides as materials for proton exchange membranes",Elsevier Sci. Ltd., *Polymer* 42 (2001) 359-373.
S.I. Kim et al, "Glass transition behaviours in aromatic poly(amic dialkyl ester) precursors with various chain rigidities" Elsevier Sci Ltd., *Polymer* 40 (1999) 2263-2270).
U.S. Appl. No. 12/770,795, filed Apr. 30, 2010, titled Semiconducting Devices and Methods of Preparing, by D. Shukla et al.
U.S. Appl. No. 12/770,798, filed Apr. 30, 2010, titled Methods of Preparing Semiconductive Compositions and Devices, by D. Shukia et al.
U.S. Appl. No. 12/770,803, filed Apr. 30, 2010, titled Aromatic Amic Acids or Amic Esters and Compositions, by D. Shukla et al.
Gao, Xike et al., "First Synthesis of 2,3,6,7-Tetrabromonaphthalene Diimide", Organic Letters 27, Sep. 2007 LNKD-PubMed: 17824615, vol. 9, No. 20.
M. Kim, et al., "Hydrolysis of aliphatic naphthalene diimides: effect of charge placement in the side chains", Journal of Physical Organic Chemistry, vol. 21, 2008, pp. 731-737.
Kheifets, G. M. et al., "Structure of hydrolysis products and position of equilibrium as a function of the pH of the medium", Zhurnal Organicheskoi Khimii, Institute of Experimental Medicine, Academy of Medical Sciences of the USSR, Leningrad, vol. 18, No. 8, Aug. 1, 1982, pp. 1528-1536.

* cited by examiner

*Primary Examiner* — Paul A Zucker
(74) *Attorney, Agent, or Firm* — J. Lanny Tucker

(57) ABSTRACT

Novel amic acids and amic esters can be thermally converted into corresponding arylene diimides. These amic acids and amic ester can be used as precursors to prepare semiconducting thin films that can be used in various articles including thin-film transistor devices that can be incorporated into a variety of electronic devices. In this manner, the arylene diimides need not be coated out of solvent in which they may be insoluble, but they can be generated in situ from a solvent-soluble, easily coated amic acid or amic ester.

8 Claims, 9 Drawing Sheets

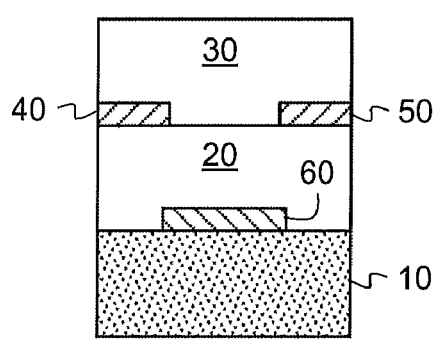
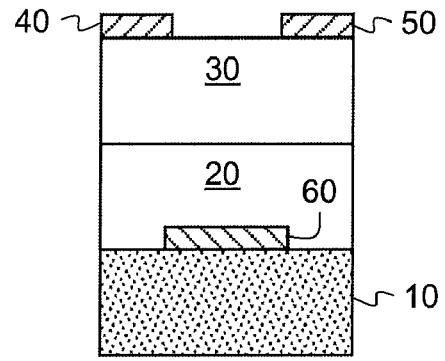
FIG. 1A  FIG. 1B
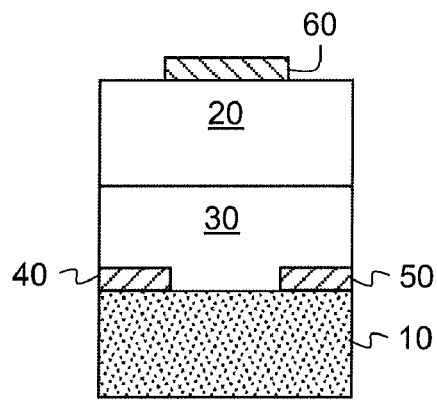
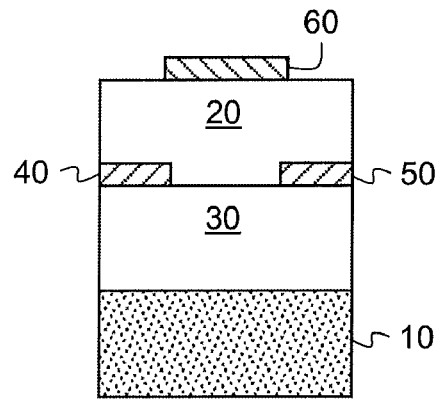
FIG. 1C  FIG. 1D excellent# AROMATIC AMIC ACIDS OR AMIC ESTERS AND COMPOSITIONS

FIELD OF THE INVENTION

This invention relates to a unique class of organic amic acid or amic esters that can be provided as compounds or compositions that are capable of being thermally converted into corresponding arylene diimides.

BACKGROUND OF THE INVENTION

Considerable efforts have been made to discover new organic semiconductor materials that can be used in FET's to provide switching or logic elements in electronic components, many of which require significant mobilities well above 0.01 $cm^2$/V·sec, and current on/off ratios (hereinafter referred to as "on/off ratios") greater than 1000. Organic FET's ("OFET's") having such properties can be used for electronic applications such as pixel drivers for displays and identification tags. Most of the compounds exhibiting these desirable properties are "p-type" or "p-channel," however, meaning that negative gate voltages, relative to the source voltage, are applied to induce positive charges (holes) in the channel region of the device.

As an alternative to p-type organic semiconductor materials, n-type organic semiconductor materials can be used in FET's where the terminology "n-type" or "n-channel" indicates that positive gate voltages, relative to the source voltage, are applied to induce negative charges in the channel region of the device.

Moreover, one important type of FET circuit, known as a complementary circuit, requires an n-type semiconductor material in addition to a p-type semiconductor material. In particular, the fabrication of complementary circuits requires at least one p-channel FET and at least one n-channel FET. Simple components such as inverters have been realized using complementary circuit architecture. Advantages of complementary circuits, relative to ordinary FET circuits, include lower power dissipation, longer lifetime, and better tolerance of noise. In such complementary circuits, it is often desirable to have the mobility and the on/off ratio of an n-channel device similar in magnitude to the mobility and the on/off ratio of a p-channel device. Hybrid complementary circuits using an organic p-type semiconductor and an inorganic n-type semiconductor are known, but for ease of fabrication, an organic n-channel semiconductor material would be desired in such circuits.

Only a limited number of organic materials have been developed for use as a semiconductor n-channel in OFET's. One such material, buckminsterfullerene C60, exhibits a mobility of 0.08 $cm^2$/V·sec but it is considered unstable in air (Haddon et al. *Appl. Phys. Let.* 1995, 67, 121). Perfluorinated copper phthalocyanine has a mobility of 0.03 $cm^2$/V·sec and is generally stable to air operation, but substrates must be heated to temperatures above 100° C. in order to maximize the mobility in this material (Bao et al. *Am. Chem., Soc.* 1998, 120, 207). Other n-channel semiconductors, including some based on a naphthalene framework, have also been reported, but with lower mobilities. One such naphthalene-based n-channel semiconductor material, tetracyanonaphthoquinodimethane (TCNNQD), is capable of operation in air, but the material has displayed a low on/off ratio and is also difficult to prepare and purify.

Aromatic tetracarboxylic diimides, based on a naphthalene aromatic framework, have also been demonstrated to provide, as an n-type semiconductor, n-channel mobilities up to 0.16 $cm^2$/V·sec using top-contact configured devices where the source and drain electrodes are on top of the semiconductor. Comparable results could be obtained with bottom contact devices, that is, where the source and drain electrodes are underneath the semiconductor, but a thiol underlayer must then be applied between the electrodes (that must be gold) and the semiconductor as described in U.S. Pat. No. 6,387,727 (Katz et al.). In the absence of the thiol underlayer, the mobility of these compounds was found to be orders of magnitude lower in bottom-contact devices. This patent also discloses fused-ring tetracarboxylic diimide compounds, one example of which is N,N'-bis(4-trifluoromethyl benzyl)naphthalene diimide. The highest mobilities of 0.1 to 0.2 $cm^2$/V·sec were reported for N,N'-dioctyl naphthalene diimide.

In a different study, using pulse-radiolysis time-resolved microwave conductivity measurements, relatively high mobilities have been measured in films of naphthalene diimides having linear alkyl side chains (Struijk et al., *J. Am. Chem. Soc.* Vol. 2000, 122, 11057).

U.S. Patent Application Publication 2002/0164835 (Dimitrakopoulos et al.) discloses n-channel semiconductor films made from perylene diimide compounds, as compared to naphthalene-based compounds, one example of which is N,N'-di(n-1H,1H-perfluorooctyl) perylene diimide. Substituents attached to the imide nitrogens in the diimide structure comprise alkyl chains, electron deficient alkyl groups, and electron deficient benzyl groups, and the chains preferably having a length of four to eighteen atoms. Devices based on materials having a perylene framework used as the organic semiconductor have low mobilities, for example $10^{-5}$ $cm^2$/V·sec for perylene tetracarboxylic dianhydride (PTCDA) and $1.5 \times 10^{-5}$ $cm^2$/V·sec for N,N'-diphenyl perylene diimide (PTCDI-Ph) (Horowitz et al. *Adv. Mater.* 1996, 8, 242 and Ostrick et al. *J. Appl. Phys.* 1997, 81, 6804).

The morphology of an organic film has a strong impact on the charge transport and overall device performance of organic thin film transistors. In general, the morphology of organic films depends directly on the chemical structure of the molecules that controls the interaction between the molecules. In crystalline organic films defects, like grain boundaries and disorder inside the grains, are limiting factors for the mobility and the diffusion length of the charge carriers. The extent of π-stacking between the molecules determines whether the organic film will be highly crystalline or totally amorphous independently of other growth controlling parameters like the substrate and its temperature.

In perylene and naphthalene diimide based OFET's, many experimental studies have demonstrated that morphology of the thin film has strong impact on the device performances. Theoretical calculation and experimental characterization (particularly X-ray diffraction), have shown that the molecular packing in PDI is very sensitive to the side chains (Kazmaier et al. *J. Am. Chem. Soc.* 1994, 116, 9684). In perylene diimide based n-channel OFET devices, changing the side chain from n-pentyl to n-octyl increases the field effect mobility of from 0.055 $cm^2$/V·sec to 1.3 $cm^2$/V·sec, respectively (Chesterfield et al. *J. Phys. Chem. B* 2004, 108, 19281). Such sensitivity to the type of side-chain is a manifestation of an aggregation effect and it provides potentially an effective way to control and optimize the molecular packing for enhanced π-orbital overlap between neighboring molecules, a necessary for efficient carrier transport. U.S. Pat. No. 7,422,777 (Shukla et al.) discloses N,N'-dicycloalkyl-substituted naphthalene diimide compounds, which in thin films, exhibit optimum packing and exhibit n-channel mobility up to 6 $cm^2$/V·sec in OFET's. U.S. Pat. No. 7,579,619 (Shukla et al.)

discloses N,N'-di(arylalkyl) substituted naphthalene diimide compounds that exhibit high n-channel mobility up to 3 cm$^2$/V·sec in top-contact OFET's.

U.S. Patent Application Publications 2008/0135833 (Shukla et al.) and 2009/0256137 (Shukla et al.) describe n-type semiconductor materials for thin film transistors that include configurationally controlled N,N'-dicycloalkyl-substituted naphthalene 1,4,5,8-bis-carboximide compounds or N,N'-1,4,5,8-naphthalenetetracarboxylic acid imides having a fluorinated substituent, respectively.

A variety of naphthalene diimides have been made and tested for n-type semiconducting properties. In general, these materials, as an n-type semiconductor, have provided n-channel mobilities up to 6 cm$^2$/V·sec using top-contact configured devices. However, besides charge mobility, improved stability and integrity of the semiconductor layer is an important goal.

A way to improve organic semiconductor layer stability and integrity in a device would be to include the organic semiconductor molecule in a polymeric additive. However, the performance of OFET's, characterized by parameters such as the field effect mobility and threshold voltage, depends in part upon the molecular structure and crystalline order of the semiconductor film. Structure and molecular ordering of the semiconductor film depends in turn on how the thin film is deposited. It is generally believed that increasing the amount of molecular order by increasing crystal size, reducing the density of crystalline defects, or improving short-range molecular order, permits charge carriers, that is, electrons or holes, to more efficiently move between molecules. This can increase the field effect mobility.

U.S. Patent Application Publication 2005/0176970 (Marks et al.) discloses improved n-channel semiconductor films made of mono and diimide perylene and naphthalene compounds, nitrogen and core substituted with electron withdrawing groups. Substituents attached to the imide nitrogens in the diimide structure can be selected from alkyl, cycloalkyl, substituted cycloalkyl, and aryl and substituted aryl moieties. However, this publication fails to suggest any comparative advantage of using cycloalkyl groups on the imide nitrogens. Accordingly, mobilities obtained from perylene diimides containing of N-octyl and N-cyclohexyl are virtually indistinguishable (Example 10). Furthermore, the highest mobilities reported in this reference were 0.2 cm$^2$/V·sec and it fails to show experimental data with respect to naphthalene compounds and require that their core be dicyano disubstituted.

Aromatic tetracarboxylic diimides, based on a naphthalene and perylene aromatic framework have been widely used as n-type semiconductor materials (Newman et al. *Chem. Mater.* 2004, 16, 4436-4451). Relatively low mobilities have been measured in films of naphthalene tetracarboxylic diimides having linear alkyl side chains using pulse-radiolysis time-resolved microwave conductivity measurements. See Struijk et al. "Liquid Crystalline Perylene Diimides: Architecture and Charge Carrier Mobilities" *J. Am. Chem. Soc.* Vol. 2000, 122, 11057. However, TFT's based on N,N'-dicyclo substituted naphthalene diimide exhibit mobility up to 5 cm$^2$/V·sec (Shukla et al. *Chem. Mater.* 2008, 20, 7486-7491). U.S. Pat. No. 6,387,727 (Katz et al.) discloses fused-ring tetracarboxylic diimide compounds, such as N,N'-bis(4-trifluoromethyl benzyl)naphthalene-1,4,5,8,-tetracarboxylic acid diimide. The highest mobilities reported in this patent is between 0.1 and 0.2 cm$^2$/V·sec, for N,N'-dioctyl naphthalene-1,4,5,8-tetracarboxylic acid diimide.

Higher carrier mobilities are obtained when naphthalene tetracarboxylic diimides are substituted with aryl groups. Accordingly, U.S. Pat. No. 7,629,605 (Shukla et al.) discloses a thin film of organic semiconductor material that comprises an N,N'-diaryl-substituted naphthalene-based tetracarboxylic diimide compound having a substituted or unsubstituted aromatic ring system directly attached to each imide nitrogen atom, wherein the substituents on at least one or both of the aromatic ring systems comprises at least one electron donating organic group. These materials consistently exhibit higher mobility compared to a naphthalene tetracarboxylic diimide having phenyl substituents.

As is clear from the foregoing discussion, the development of new semiconducting materials, both p-type and n-type, continues to be an enormous topic of interest and unpredictable as to the semiconductive properties of various compounds. Among n-type diimide based materials, the highest charge carrier mobility (ca. 5.0 cm$^2$/V·sec) in thin film transistors has been observed with N,N'-dicyclohexyl-naphthalene diimide. However, the poor solubility of this material limits its practical application potential.

Recently, dicyanated arylene diimide semiconductors based on perylene and naphthalene diimide cores have been developed that are solution processable and show environmental stability (*Adv. Funct. Mater.* 2008, 18, 1329-1339). The latter characteristics arise from cyano group addition to the core, which increases solubility by decreasing molecular planarity and stabilizes charge carriers by lowering the energies of the lowest unoccupied molecular orbital's associated with electron transport. While high temperature vapor deposited devices using these materials show good mobilities (ca. 0.1-0.5 cm$^2$/V·sec; Jones et al. *Adv. Funct. Mater.* 2008, 18, 1329-1339), solution coated device usually give lower mobility and exhibit low $I_{on}/I_{off}$ ratio.

It is widely recognized that the morphology and microstructure of an organic thin film has a strong impact on the charge carrier mobility and OTFT device characteristics. In general, organic materials that form highly oriented polycrystalline thin films exhibit high charge carrier mobility. At the molecular level, it is the basic chemical structure of the molecule that controls intermolecular interactions that determines if a material will be crystalline or amorphous. Thus, to have well-defined thin film morphology it is necessary to control materials on the molecular scale. This necessitates adapting the basic structure of semiconducting molecules in a way that results in an optimum crystalline packing motif. In the case of diimide based n-type semiconducting materials to attain solubility extensive molecular modification have to be made which usually lowers the crystallinity of the material (for example see et al. *Adv. Funct. Mater.* 2008, 18, 1329-1339) that usually results in lower mobility in OTFT devices.

Efforts are continuing to improve performance of n-type organic semiconductor materials in OTFT's and technology for their manufacture and use. Specifically there continues to be research efforts to find new materials and processes that are useful in n-type semiconducting materials which compounds do not require significant structural modification to achieve processability and optimum crystalline packing.

Amic acids are usually more soluble in solvents than the aromatic anhydrides that they are derived from. One attractive way of obtaining diimide based semiconductors in thin solid films is to solution coat amic acid and then by a thermal dehydration reaction, convert the amic acid to the corresponding diimide.

The dehydration of amic acids, derived from the reaction of cyclic anhydrides with primary amines, to yield imides is a general method for the preparation of this important class of heterocyclic compounds and is of major commercial significance in the conversion of polyamic acids to polyimides (J. A.

Kreuz, A. L. Endrey, F. P. Gay, and C. E. Sroog, *J. Polym. Sci., Part A*, 4, 2607 (1966), and references contained therein.). As polyimides derived from phthalamic acids possess many desirable attributes, this class of materials have found uses in many technologies including dielectrics in microelectronics, high temperature adhesives, and membranes (for example, see K. L. Mittal, *Polyimides and Other High Temperature Polymers: Synthesis, Characterization and Applications* vol. 1 to 5). Most of the detailed studies have concentrated on the preparation of polyphthalamic acids and their conversion to polyimides in solid films (for example see Kim et al. in *Polymer* 40, 1999, pp 2263-2270, and references cited therein). In contrast, little is known about the dehydration reactions of amic acids derived from naphthalene and perylene anhydrides or naphthalene and perylene tetracarboxylic acid dianhydrides. Fabienne et al. have recently reported mechanistic studies of polycondensation reactions of naphthalene anhydride leading to naphthalimide polymers (Piroux, Fabienne; Mercier, Regis; Picq, Dominique, *High Performance Polymers* (2009), 21(5), 624-632). However, these authors do not disclose amic acids and amic esters of naphthalene tetracrboxylic acids or anhydrides.

Genies et al. have reported synthesis of soluble sulfonated naphthalenic polyimides, derived from naphthalene dianhydride, as materials for proton exchange membranes (Genies et al., *Polymer* 42 (2001) 359-373). However, these authors do not disclose the preparation of amic acid or amic ester from naphthalene dianhydride.

SUMMARY OF THE INVENTION

This invention provides an organic composition that comprises new amic acids and amic esters. Such compositions can consist only of the amic acid and amic ester compounds, or such compounds can be provided in solution form with one or more solvents.

In particular, the amic acid or amic ester is an arylene tetracarboxylic acid or ester precursor is represented by the following Structure (I), (II), or (III):

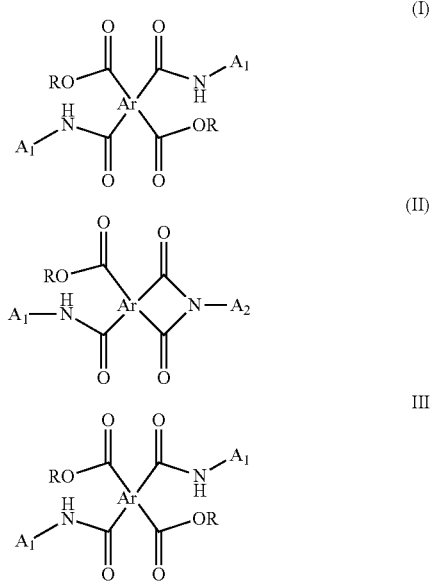

wherein Ar is an anthracene, naphthalene, or perylene nucleus and the four carbonyl groups are attached directly to peri carbon atoms, $A_1$ and $A_2$ are independently aryl, heteroaryl, non-aromatic alkyl, alkylaryl, fluoroalkyl, cycloalkyl, or heterocyclyl groups, and R is hydrogen or an alkyl or cycloalkyl group that can be the same or different as that defined for $A_1$ and $A_2$.

The compounds of this invention can be used to prepare thin films that are thermally convertible to corresponding semiconductive arylene diimide compounds, such as, naphthalene diimide. Thus, the arylene diimides are obtained via solid state thermal dehydration imidization reaction of the organic-soluble precursor amic acids or amic esters of diimide compounds. The amic acids and amic esters can be easily prepared in environmentally friendly solvents like methanol, ethanol, water, or mixtures thereof.

The advantages of these invention are achieved by preparing thin films of semiconducting arylene diimides by solid state thermal dehydration imidization reaction of amic acid or amic ester precursor or mixture thereof. The low temperature processing combined with readily available materials and ease of deposition of thin films over large areas due to solubility of the amic acids and amic esters provide an inexpensive approach to the fabrication of thin film transistor devices.

Furthermore, since corresponding diimides, amic acids, and amic esters are readily soluble in a variety of solvent (especially organic solvents), this invention provides for coating the amic acids and amic esters on a variety of substrates without additional preparation such using adhesion promoters or adhesive layers, or by using surface modification techniques.

The present invention and its advantages will become more apparent when taken in conjunction with the following description, drawings, and the illustrative working examples provided below.

BRIEF DESCRIPTION OF THE DRAWINGS

FIGS. 1a through 1d illustrate cross-sectional views of four possible configurations for an organic field effect transistor. FIGS. 1a and 1b have a bottom gate configuration and FIGS. 1c and 1d have a top gate configuration

DETAILED DESCRIPTION OF THE INVENTION

Definitions

Figure 2A:
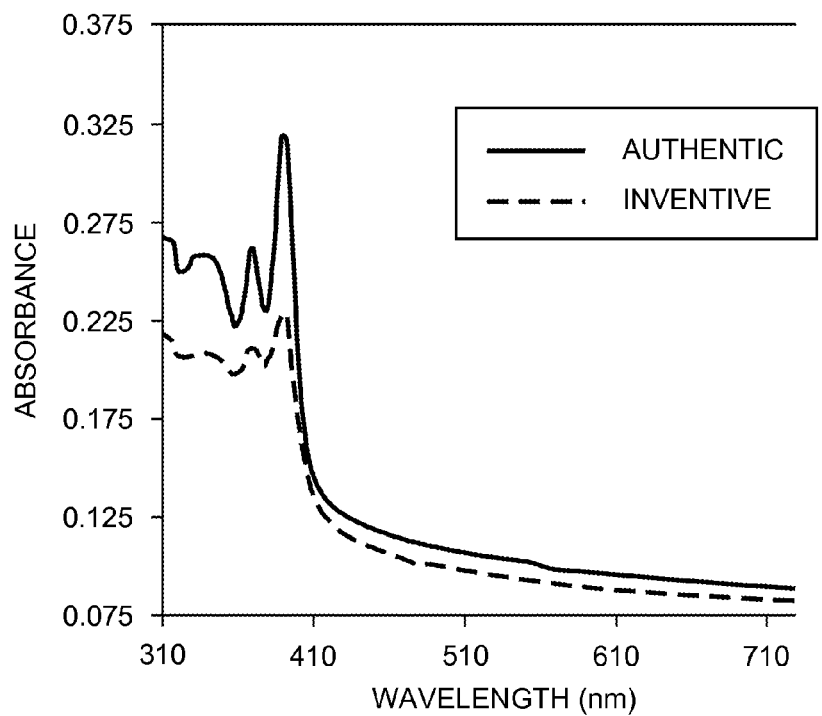
FIGS. 2A, 2B, 2C, and 2D are graphical plots that provide analytical characterizations used in Invention Example 1 below.

As used herein, "a" or "an" or "the" are used interchangeably with "at least one," to mean "one or more" of the components or elements being defined. For example, mixtures of amic acid or ester precursors can be used to provide mixtures of arylene diimide compounds.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituents unsubstituted form, but also its form to the extent it can be further substituted (up to the maximum possible number) with any other mentioned substituent group or groups (mentioned for the same position) so long as the substituent does not destroy properties necessary for semiconductor utility. If desired, the substituents can themselves be further substituted one or more times with acceptable substituent groups. When a molecule can have two or more substituents, the substituents can be joined together to form an aliphatic or unsaturated ring unless otherwise provided.

Amic Acid and Amic Ester Compounds and Compositions n-Channel organic semiconductor layers (or thin films) can include one or more of arylene diimide compounds described herein. This layer is capable of exhibiting a field effect electron mobility that is greater than 0.001 cm$^2$/V·sec, or greater than 0.1 cm$^2$/V·sec, or more likely greater than 1 cm$^2$/V·sec. In many useful embodiments, the thin organic semiconductor films (and the devices containing the films) exhibit a field effect electron mobility that is greater than 0.25 cm$^2$/V·sec.

In addition, the n-channel organic semiconductor film is capable of providing on/off ratios of a source/drain current of at least 10$^4$ or typically of at least 10$^5$. The on/off ratio is measured as the maximum/minimum of the drain current as the gate voltage is swept from zero to 100 volts and the drain-source voltage is held at a constant value of 100 volts, and employing a gate dielectric.

Moreover, these properties are attainable after repeated exposure of the n-type organic semiconducting layer to air before layer deposition as well as exposure of the thin film transistor device or the channel layer to air after layer deposition.

Without wishing to be bound by theory, there are several factors that are believed to contribute to the desirable properties of the organic semiconductor layer containing arylene diimides compounds. The solid-state structure of the arylene diimide compounds described herein exhibit good order in the layer. The molecules are packed such that the orbital's of the conjugated arylene core system containing the arylene ring system or the imide carboxyl groups are able to interact with adjacent molecules, resulting in high mobility. The direction of this interaction has a component parallel to the direction of desired current flow in a device using this material in the semiconductor layer. The morphology of the layer formed by arylene diimides is substantially continuous such that current flows through the material without unacceptable interruption. However, it is particularly advantageous that the arylene diimide layer is not only continuous but also exhibits polycrystalline morphology with minimum inter-grain defects so that current flows through the material without unacceptable interruption. The stereochemistry of the substituent on the arylene diimides is such that they do not disrupt the intrinsic ability of these molecules to pack in an effective crystalline arrangement.

The lowest lying unoccupied molecular orbital of the arylene diimide compound is at an energy that allows for injection of electrons in the compound at useful voltages from metals with reasonable work functions. Arylene diimides (such as naphthalene diimides and perylene diimides) described herein have a desirable lowest unoccupied molecular orbital (LUMO) energy level of about 3.0 eV to about 4.6 eV with reference to the vacuum energy level. As known in the art, LUMO energy level and reduction potential approximately describe the same characteristics of a material. LUMO energy level values are measured with reference to the vacuum energy level, and reduction potential values are measured in solution versus a standard electrode. An advantage for thin film transistor devices is that the LUMO in the crystalline solid, which is the conduction band of the organic semiconductor, and the electron affinity of the solid both are measured with reference to the vacuum level. The latter parameters are usually different from the former parameters, which are obtained from solution.

As indicated above, the organic solvent-soluble compositions comprise one or more amic acids or amic esters that can be converted with thermal energy to provide organic semiconductor compositions having one or more of the corresponding arylene diimides compounds. In many embodiments, the organic semiconductor layer provided by the invention consists essentially of the one or more arylene diimide compounds, meaning that no other components are present that are essential to semiconductivity. Still other embodiments of this invention have thin film semiconductor layers that consist only of the one or more arylene diimide compounds, which compounds are derived from the thermal conversion of the corresponding amic acids or amic esters.

The amic acid and amic ester compositions of this invention offer several advantages. For example, since the amic acids and amic esters are soluble in a number of organic solvents, they can be deposited on the surface of a given substrate from a suitable organic solvent solution without any additional surface preparation (for example, surface energy matching). In cases where the substrate is polymeric, the solutions can be prepared using organic solvents or mixtures of solvents that do not have unfavorable or undesirable interaction (for example, swelling) with the substrate.

In some embodiments of this invention (organic compounds and compositions) the arylene diimide compounds present in the thin film semiconductor layer are thermal dehydration imidization products of arylene tetracarboxylic acid or ester precursors that are represented by the following Structure (I):

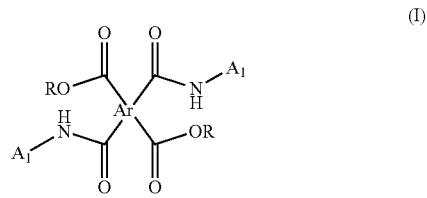

(I)

wherein Ar is a substituted or unsubstituted anthracene, naphthalene, or perylene nucleus and the four carbonyl groups are attached directly to peri carbon atoms, $A_1$ is an aryl, heteroaryl, alkyl (including alkylaryl and non-aromatic alkyl groups), fluoroalkyl, cycloalkyl, or heterocyclyl group, and R is hydrogen or an alkyl or cycloalkyl group, and can be the same or different as $A_1$.

More specifically, Ar is a substituted or unsubstituted anthracene, naphthalene, or perylene nucleus and the four carbonyl groups are attached directly to peri carbon atoms.

$A_1$ can be a substituted or unsubstituted aryl group having 6 or 14 carbon atoms in the aromatic ring (such as substituted or unsubstituted phenyl or naphthyl groups), a heteroaryl group having 5 to 10 carbon and heteroatoms (such as nitrogen, oxygen, and sulfur) in the aromatic ring (such as substituted or unsubstituted thienyl, furanyl, pyridyl, pyrrolyl, and pyrazolyl groups), a branched or linear, substituted or unsubstituted alkyl group having 1 to 18 carbon atoms and including substituted or unsubstituted fluoroalkyl groups (such as $CF_3$ or $C_3F_7$) and alkylaryl groups (such benzyl groups), a substituted or unsubstituted cycloalkyl group at least 4 carbon atoms in the carbocyclic ring, or a substituted or unsubstituted heterocyclyl group having 5 to 10 carbon and heteroatoms (such as nitrogen, oxygen, and sulfur) in the heterocyclic ring.

Various substituents on these Ar and $A_1$ groups would be readily apparent to one skilled in the art but can include for example, alkyl groups having 1 to 6 carbon atoms (such as methyl, ethyl, pentyl, and hexyl groups), cyano, fluoro, and fluoroalkyl groups (such as $CF_3$).

R is hydrogen or a substituted or unsubstituted, linear or branched alkyl group having 1 to 20 carbon atoms, including alkylaryl groups such as benzyl. Substituents for the R groups can include those defined above for Ar and $A_1$.

Some of the desired alkylaryl groups are described in U.S. Pat. No. 7,579,619 B2 (Shukla et al.) and U.S. Pat. No. 7,198,977 B2 (Shukla et al.) that are incorporated herein by reference. Some desirable fluorinated aryl groups are described in U.S. Pat. No. 7,326,956 B2 (Shukla et al.) that is also incorporated herein by reference.

Some desirable cycloalkyl groups are described in U.S. Pat. No. 7,422,777 B2 (Shukla et al.) and U.S. Pat. No. 7,649,199 B2 (Shukla et al.) that are incorporated herein by reference. Some desirable aryl groups are described in U.S. Pat. No. 7,629,605 B2 (Shukla et al.) that is incorporated herein by reference.

In most embodiments of the Structure (I) compounds, Ar is a substituted or unsubstituted naphthalene or perylene, $Ar_1$ is a substituted or unsubstituted alkyl, substituted or unsubstituted fluoroalkyl, substituted or unsubstituted alkylaryl, substituted or unsubstituted phenyl, or substituted or unsubstituted cycloalkyl group, and R is hydrogen or a substituted or unsubstituted methyl or ethyl group. More likely, Ar is perylene, $A_1$ is a substituted or unsubstituted alkyl group of 1 to 12 carbon atoms, phenyl, substituted or unsubstituted ($C_1$-$C_3$)alkylphenyl, substituted or unsubstituted cyclopentyl, or substituted or unsubstituted cyclohexyl group, and R is hydrogen or a substituted or unsubstituted methyl group.

In other embodiments of this invention (organic compounds and compositions), the arylene diimide compounds are thermal dehydration imidization products of corresponding arylene tetracarboxylic acid or ester precursors that are represented by the following Structure (II):

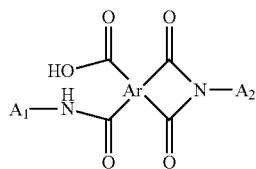

wherein Ar and R are as defined above for Structure (I).

$Ar_1$ and $Ar_2$ are independently the groups used above for the definition of $Ar_1$ for Structure (I). In many embodiments, $Ar_1$ and $A_2$ are the same type of group, such as a substituted or unsubstituted alkyl group (but they can be different alkyl groups). In most embodiments, they are the same group, such as the same substituted or unsubstituted alkyl group. For example, $A_1$ and $A_2$ can be the same or different substituted or unsubstituted, linear or branched alkyl group having 1 to 18 carbon atoms, a substituted or unsubstituted cycloalkyl group having 4 to 10 carbons in the alicyclic ring, including unbridged monocyclic or bridged bicyclic ring systems as defined above for $A_1$ for Structure (I).

For example, Ar can be a substituted or unsubstituted naphthalene or perylene group and $A_1$ and $A_2$ are the same substituted or unsubstituted non-aromatic alkyl, alkylaryl, fluoroalkyl, alkylphenyl, phenyl, or cycloalkyl groups.

Some desirable alkylaryl groups are described in U.S. Pat. No. 7,579,619 B2 and U.S. Pat. No. 7,198,977 B2 (both noted above). Some desirable fluorinated aryl groups are described in U.S. Pat. No. 7,326,956 B2 (noted above). Some desirable cycloalkyl groups are described in U.S. Pat. No. 7,422,777 B2 and U.S. Pat. No. 7,649,199 B2 (both noted above). Some desirable aryl groups are described in U.S. Pat. No. 7,629,605 B2 (noted above).

Still other embodiments of this invention (organic compounds and compositions), the arylene diimide compounds are thermal dehydration imidization products of corresponding arylene tetracarboxylic acid or ester precursors that are represented by the following Structure (III):

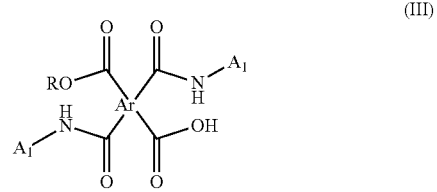

wherein Ar, $A_1$, and R are defined as described above for Structure (I). In many embodiments of Structure (III) compounds, Ar is a substituted or unsubstituted naphthalene or perylene, and $A_1$ is a substituted or unsubstituted alkyl, fluoroalkyl, alkylphenyl, phenyl, or cycloalkyl group.

Some desirable alkylaryl groups are described in U.S. Pat. No. 7,579,619 B2 and U.S. Pat. No. 7,198,977 B2 (both noted above). Some desirable fluorinated aryl groups are described in U.S. Pat. No. 7,326,956 B2 (noted above). Some desirable cycloalkyl groups are described in U.S. Pat. No. 7,422,777 B2 and U.S. Pat. No. 7,649,199 B2 (both noted above). Some desirable aryl groups are described in U.S. Pat. No. 7,629,605 B2 (noted above).

Examples of amic acids and amic esters of this invention are listed below as compounds I-1 through I-50:

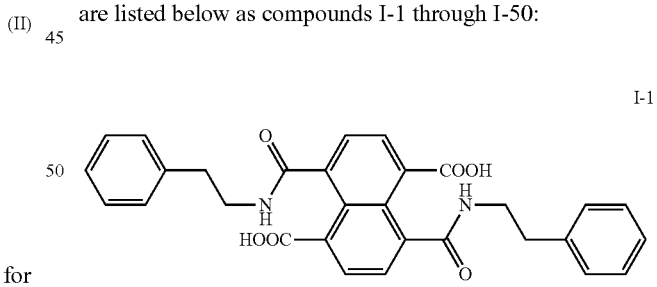

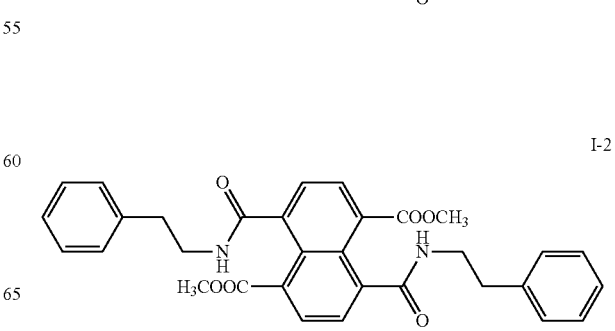

I-19
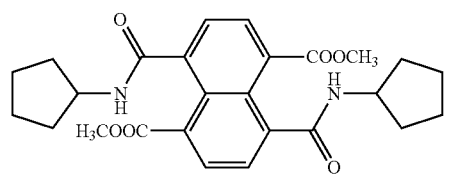
I-20
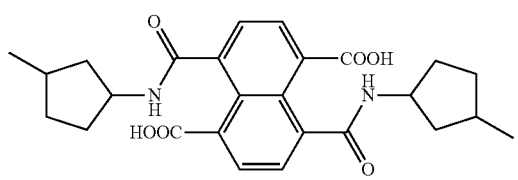
I-21
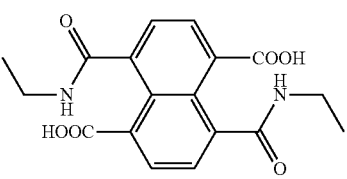
I-22
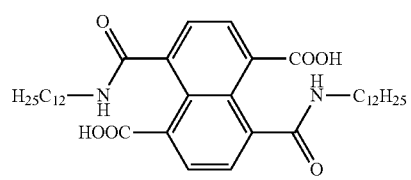
I-23
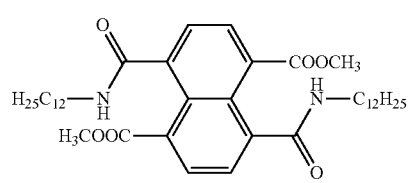
I-24
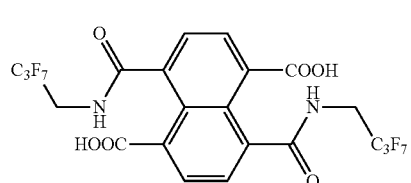
I-25
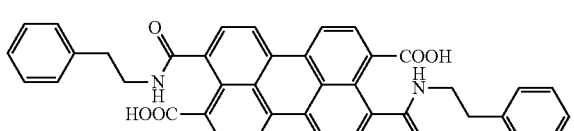
I-26
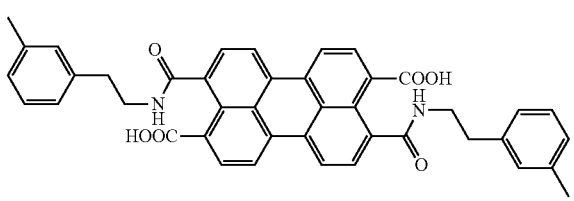
I-27
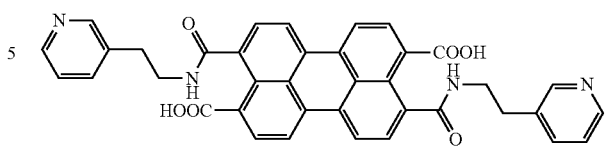
I-28
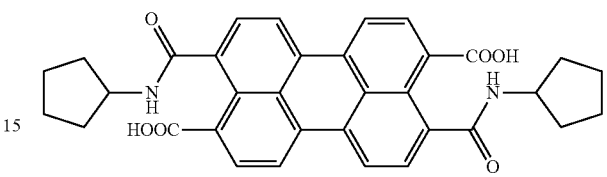
I-29
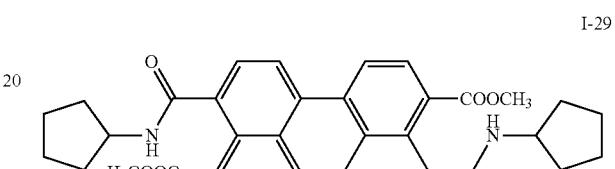
I-30
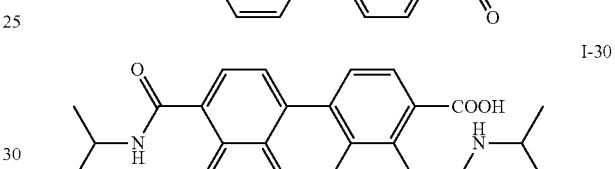
I-31
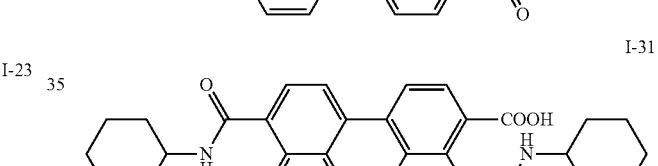
I-32
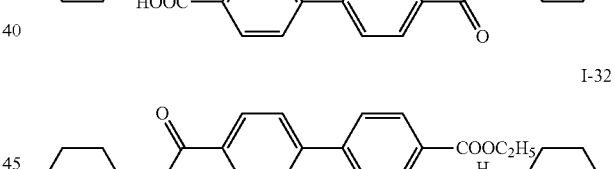
I-33
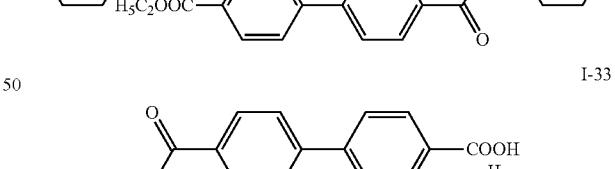
I-34
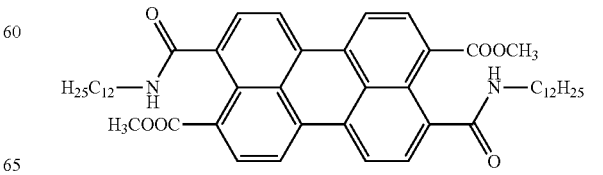

I-35
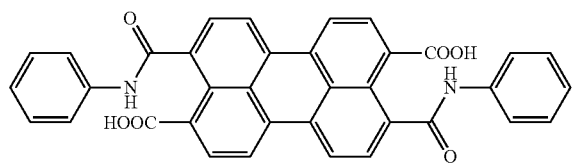
I-36
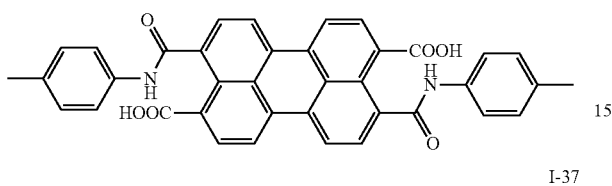
I-37
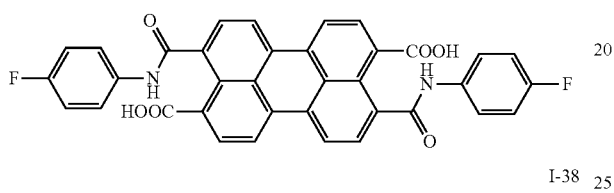
I-38
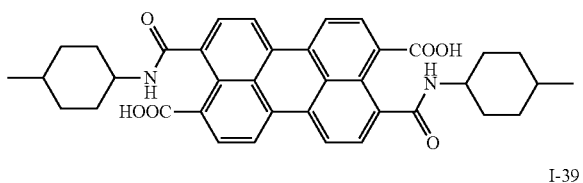
I-39
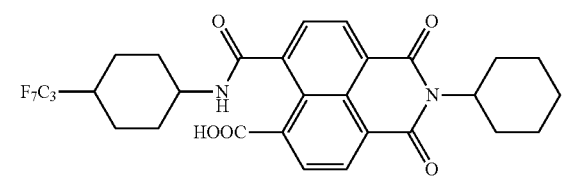
I-40
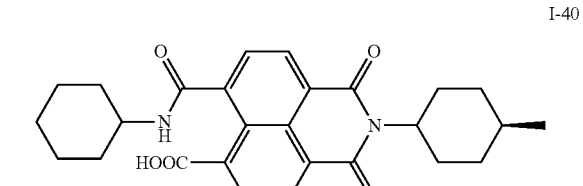
I-41
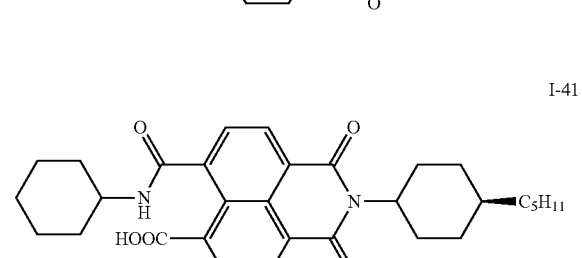
I-42
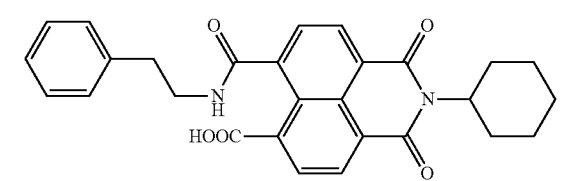
I-43
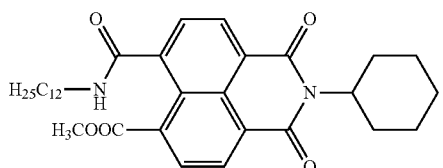
I-44
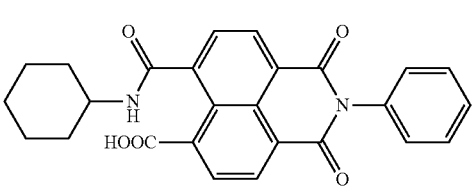
I-45
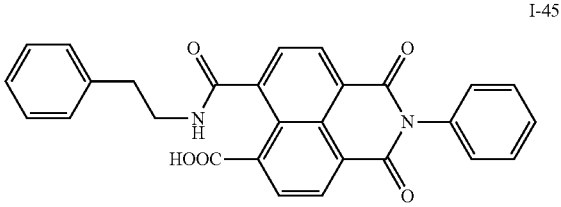
I-46
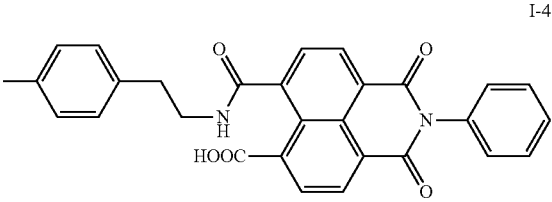
I-47
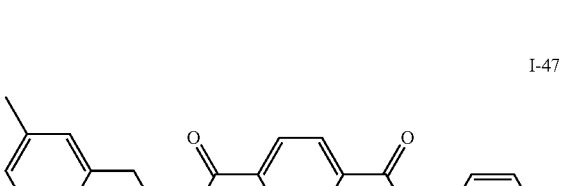
I-48
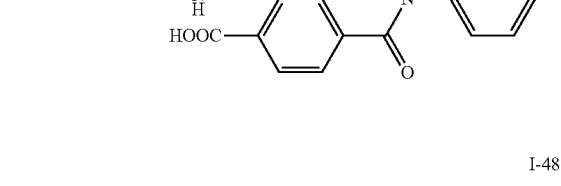
I-49
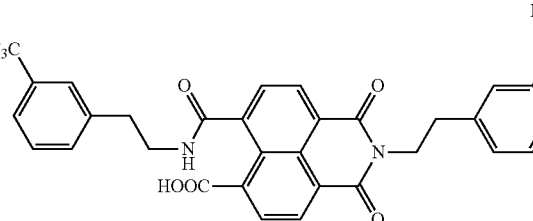

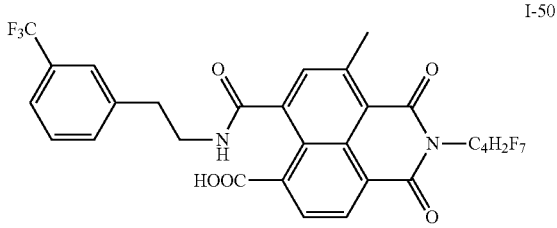

I-50

The amic acids or amic ester of this invention can be easily prepared in a single step reaction scheme, and the syntheses of several compounds are described below in the Examples.

A tetracarboxylic acid or its derivative can be used to obtain a specific amic acid or ester precursor. Specific examples include but are not limited to, aromatic tetracarboxylic acids such as 1,4,5,8-naphthalene tetracarboxylic acid, 3,4,9,10-perylene tetracarboxylic acid, 1,5,9,10-anthracene tetracarboxylic acid, and their dianhydrides and their dicarboxylic diacid halides;

The amic acid can be prepared by a simple, one step conventional reaction that is well known to those skilled in the art. For example, bisnaphthalamic acid can be prepared by reacting an appropriate primary amine with naphthalene dianhydride or the corresponding naphthalene tetracarboxylic acid at ambient temperature in a suitable solvent or mixtures of solvents. Similar reactions can easily be carried out using other bisanhydrides and carboxylic acids.

A number of organic solvents can be used for the reactions of the tetracarboxylic acid or dianhydride with the amine and the choice of solvent is not particularly limited so long as it dissolves the amic acid product. Specific examples include methanol, ethanol, n-propanol, n-butanol, N,N-dimethylformamide, N,N-dimethylacetamide, N-methyl-2-pyrrolidone, N-methylcaprolactam, dimethyl sulfoxide, tetramethylurea, pyridine, dimethyl sulfone, hexamethyl sulfoxide, and γ-butyrolactone. These solvents can be used alone or in combination. Any of these solvents can also be used in combination with water. Even an organic solvent that is incapable of dissolving an amic acid, can be used in combination with a solvent in which it is soluble so long as the amic acid produced will not be precipitated. In most instances, the amic acid or amic ester has a solubility in at least one of the solvents (and typically many of the solvents) of at least 0.01 g/ml at room temperature and atmospheric pressure. The specific solvent to be used will depend upon the intended use of the amic acid and amic ester, and would be readily determined by one skilled in the art with routine experimentation.

When prepared in hydroxylic solvents like methanol, ethanol, propanol, and other alcohols, the amic acid may be present along with the amic ester derived from the hydroxylic solvent. For example Equation 1 below shows the formation of an ester along with the amic acid, when an amic acid is prepared starting from a bisanhydride and an amine $A_1NH_2$ in a solvent ROH:

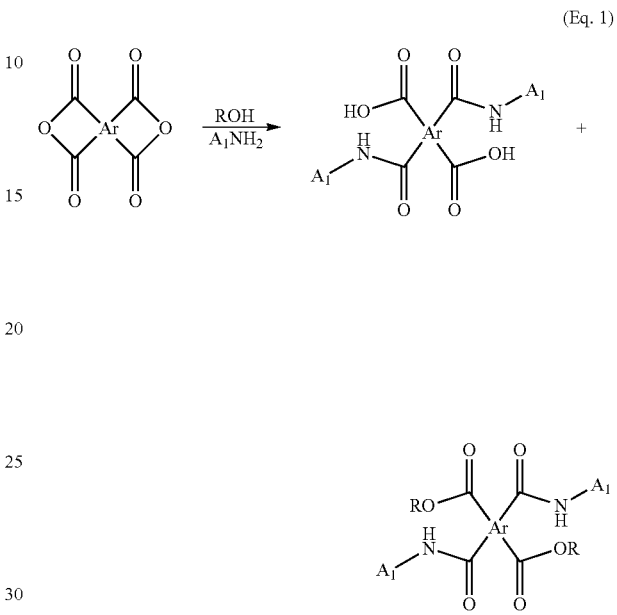

(Eq. 1)

The relative ratios of amic acid to amic ester depend on a number of variables like the nature of the alcohol solvent, the presence of an acid or base catalyst, reaction temperature, and the duration of reaction.

Furthermore, in solution, the amic acid may exist in equilibrium with tetrahedral intermediates T1 and T2 (see the following Equation 2):

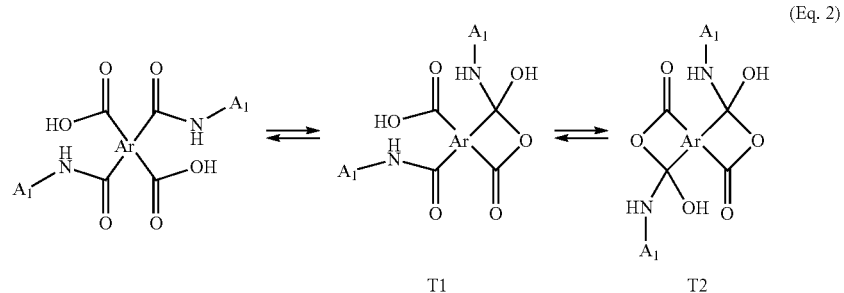

(Eq. 2)

The relative extent to which T1 and T2 may be present depends upon a number of factors (see Kluger et al., *Journal of the American Chemical Society,* 23, 1979, page 6976)

To facilitate the reaction of the tetracarboxylic acid or dianhydride with the amine component in the organic solvent, the amine component can be dispersed or dissolved in the organic solvent, under stirring, and the tetracarboxylic acid or dianhydride is then added, as it is or after dispersing or dissolving it in the organic solvent. Alternatively, the amine component can be added to a solution of the tetracarboxylic dianhydride that is dispersed or dissolved in the organic solvent. In still another method, the tetracarboxylic dianhydride and the amine component can be added simultaneously to the organic solvent. In addition, the two reactants can be added alternatively to the organic solvent until all of the desired amounts are in the solution or dispersion. Stirring or other suitable agitation may be desirable to obtain a solution or dispersion of the reactants. A skilled worker would understand that still other procedures can be used to obtain the desired reaction product.

In the preparation of the amic acid or amic ester, the molar ratio of the amine reactant (that is, the total moles of the amine to the tetracarboxylic dianhydride) is generally at least 2:1, or at least 2.5:1, or more likely at least 3:1.

Depending on the nature of the amine and dianhydride or carboxylic acid, the described synthesis of the amic acid or amic ester can be carried out at very low temperatures (from −20 to 0° C.), at room temperature, or at a higher temperature of from 25 to 100° C. The reaction of bisanhydride with the amine proceeds to give the amic acid, amic ester, or a mixture of an amic acid and amic ester, in high yield. For this reason, the reaction can easily be scaled up to any desired concentration. Accordingly, the concentration of the resulting product is generally from 1 to 50 wt. % or from 5 to 30 wt. %, or even from 1 to 10 wt. % in the reaction solution or dispersion. The reaction can be carried out at a high concentration in the initial stage, and thereafter, more organic solvent, water, or both, can be added to the reaction solution or dispersion to adjust the concentration.

The amic acid or amic ester is easily converted to the corresponding arylene diimide compound by thermal dehydration imidation ring closure reaction. The temperature of the dehydration imidation ring closure is dependent on the structure of the amic acid or amic ester. However, the thermal imidation of the amic acid or amic ester in an article or thin film transistor device is generally carried out in the solid state at a temperature of from about 100° C. to about 400° C., or from about 120° C. to about 250° C.

It is also possible to carry out a dehydration imidation ring closure reaction at lower temperatures in the presence of an added catalyst in the reaction solution or dispersions. Such catalysts include but are not limited to, basic catalysts such as pyridine, triethylamine, trimethylamine, tributylamine, diazabicyclo[1.1.1]octane, diazabicycloundecane, and trioctylamine, and acid anhydrides such as acetic anhydride, trimellitic anhydride, or pyromellitic anhydride. Catalytic imidation in which the imidation reaction proceeds at a relatively low temperature is particularly desirable. The catalyst is present in an amount of at least 0.5 weight % based on the weight of the amic acid or amic ester, or more likely from about 0.5 to about 2 weight %, based on the amic acid or amic ester that is to be thermally converted.

For example, a thin film of an arylene diimide compound can be prepared with a method comprising the steps of:

A) adding a dianhydride (as described above) to an organic solvent (described above) and stirring the resulting mixture to obtain a solution or dispersion, B) adding an amine to the dianhydride solution or dispersion and mixing the reactants to obtain an arylene diimide precursor that is an amic acid or amic ester precursor, C) applying the dianhydride solution to a suitable substrate (as described below and particularly a metal, silicon, plastic film, glass sheet, or coated glass) to form a coating, D) removing the organic solvent from the coating to form a thin film of the amic acid or amic ester precursor, and E) thermally converting (as described above) the arylene diimide precursor in the thin film to an arylene diimide compound to form an organic semiconductor layer that is generally a thin film of from about 100 to about 1000 Angstroms in dry thickness.

The solvent, or mixture of solvents, can be removed in step D using any suitable technique and equipment. Generally, the solvents are removed from the coating by a suitable evaporation technique at desired time and temperature. Higher temperatures can be used in shorted times, but it depends upon the vapor pressure of the organic solvents.

A method for preparing a thin film of an arylene diimide precursor also comprises the steps of:

A) adding a dianhydride to an organic solvent and stirring the resulting mixture to obtain a solution or dispersion, B) adding an amine to the dianhydride solution or dispersion and mixing the reactants to obtain an arylene diimide precursor that is an amic acid or amic ester precursor, C) applying the dianhydride solution to a substrate (as described below) to form a coating (or thin film), and D) removing the organic solvent from the coating to form a layer (or thin film) of the arylene diimide precursor, for example by evaporation or other technique as described above.

The resulting thin film of the amic acid or amic ester precursor (or mixture one or more amic acids and one or more amic esters) can then be further processed or used in a suitable manner before it is thermal converted to the corresponding arylene diimide compound.

More particularly, a method comprises, not necessarily in order, the following steps:

A) providing an electrically conductive substrate (as described below),

B) providing a gate electrode material over the substrate,

C) providing a gate dielectric over the gate electrode material,

D) depositing a organic solvent solution or dispersion of an arylene diimide precursor that is an amic acid or amic ester precursor over the gate dielectric, E) evaporating the organic solvent to produce a thin film of the arylene diimide precursor.

Thin films of the amic acid or amic ester can be cast or coated from solution in which they are prepared and they can be converted to the arylene diimide compound as a thin film by simply heating the substrate on which it is coated.

The amic acid or amic ester can be applied or deposited onto a suitable support using any suitable technique and equipment. For example, it can be applied out of the solution using solution coating techniques (such as spin or hopper coating), solution-phase deposition, ink jet techniques, lithographic or flexographic deposition in desired patterns, or spray coating.

Thermal Conversion of Precursor to Semiconductive Compound

The thermal conversion can be carried out using various procedures and apparatus to supply the desired thermal energy (or heat) to the precursor that is on a substrate. For example, the desired thermal energy can be provided by one or more lasers such as those emitting infrared radiation, microheaters, microwave heaters, and other heating devices that would be readily apparent to one skilled in the art. The thermal energy can be applied in a uniform manner over the entire applied coating of amic acid or amic ester, or the thermal energy can be applied patternwise to convert only a pattern of the precursor, and the non-converted precursor can then be removed in a suitable fashion (for example, by washing with a solvent in which it is soluble).

Electronic Devices

The organic semiconductor composition described herein, when used in the form of an n-channel layer, can exhibit high performance under inert conditions as well as in air without the need for special chemical underlayers.

The electronic devices comprise the thin film or organic semiconductor layer described above. The electronic devices can include, but are not limited to, an organic field effect transistor (OFET), organic light emitting diode (OLED), photodetector, sensor, logic circuit, memory element, capacitor, and photovoltaic (PV) cell. For example, the active semiconductor channel between the drain and source in an OFET can comprise the organic semiconducting layer. As another example, an electron injection or transport layer in an OLED device-can comprise the organic semiconducting layer. The amic acid or amic ester compositions of this invention and organic semiconductor layers formed there from have particular utility in OFET's.

The compounds of this invention can be used in a process for the production of semiconductor components and electronic devices incorporating such components. In one embodiment, a substrate is provided and a layer of the amic acid or amic ester composition can be applied to the substrate and electrical contacts made with the layer. The exact process sequence is determined by the structure of the desired semiconductive article. Thus, in the production of an organic field effect transistor, for example, a gate electrode can be first deposited on a flexible substrate, for example an organic polymer film, the gate electrode can then be insulated with a dielectric and then source and drain electrodes and a layer of the amic acid or amic ester can be applied on top and then thermally converted to an n-channel semiconductor layer containing the corresponding arylene diimide compound. The structure of such a thin film transistor and hence the sequence of its production can be varied in the customary manner known to a person skilled in the art. Thus, alternatively, a gate electrode can be deposited first, followed by a gate dielectric, then the amic acid or amic ester precursor layer can be applied, and finally the contacts for the source electrode and drain electrode deposited on the precursor layer, which is then thermally converted to an organic semiconductor layer containing the corresponding arylene diimide compound. A third structure could have the source and drain electrodes deposited first, then the amic acid or amic ester layer, with dielectric and gate electrode, is deposited on top. This layer can then be thermally converted in a suitable manner to provide the organic semiconductor arylene diimide compound.

The skilled artisan will recognize other structures can be prepared or intermediate surface modifying layers can be interposed between the above-described components of a thin film transistor device. In most embodiments, a field effect thin film transistor device comprises an insulating layer, a gate electrode, an organic semiconductor layer comprising an organic semiconducting arylene diimide compound (thermally converted from the amic acid or ester) as described herein, a source electrode, and a drain electrode, wherein the insulating layer, the gate electrode, the organic semiconductor layer, the source electrode, and the drain electrode are in any sequence as long as the gate electrode, and the organic semiconductor layer both contacts the insulating layer, and the source electrode and the drain electrode both contact the organic semiconductor layer.

Substrate

A substrate (also known herein as a support) can be used for supporting the organic semiconductor thin film during manufacturing, testing, or use. The skilled artisan will appreciate that a substrate selected for commercial embodiments can be different from one selected for testing or screening various embodiments. In other embodiments, a substrate can be detachably adhered or mechanically affixed to a substrate, such as when the substrate is desired for a temporary purpose. For example, a flexible polymeric substrate can be adhered to a rigid glass support, which support could be removed. In some embodiments, the substrate does not provide any necessary electrical function for the FET. This type of substrate is considered a "non-participating substrate".

Useful substrate materials can include organic or inorganic materials. For example, the substrate can comprise inorganic glasses, ceramic foils, polymeric materials, filled polymeric materials, coated metallic foils, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS), and fiber-reinforced plastics (FRP).

A flexible substrate is used in some embodiments to allow for roll processing, which can be continuous, providing economy of scale and economy of manufacturing over flat or rigid substrates. The flexible substrate chosen is capable of be wrapped around the circumference of a cylinder of less than about 50 cm diameter, typically less than 25 cm diameter, or even less than 10 cm diameter, without distorting or breaking, using low force such as by unaided hands. The flexible substrate can be rolled upon itself.

In some embodiments of the articles, the substrate is optional. For example, in a top construction as in FIG. 1b, when the gate electrode or gate dielectric provides sufficient substrate for the intended use of the resultant TFT, the substrate is not required. In addition, the substrate can be combined with a temporary support. In such an embodiment, a substrate can be detachably adhered or mechanically affixed to the substrate, such as when the substrate is desired for a temporary purpose, for example, manufacturing, transport, testing, or storage. For example, a flexible polymeric substrate can be adhered to a rigid glass support, which flexible substrate can be removed.

Gate Electrode

The gate electrode can be any useful conductive material. A variety of gate materials known in the art, are also suitable including metals, degenerately doped semiconductors, conducting polymers, and printable materials such as carbon ink or silver-epoxy. For example, the gate electrode can comprise doped silicon, or a metal, such as aluminum, chromium, gold, silver, nickel, palladium, platinum, tantalum, and titanium. Conductive polymers also can be used, for example polyaniline, poly(3,4-ethylenedioxythiophene)/poly(styrene sulfonate) (PEDOT:PSS). In addition, alloys, combinations, and multilayers of these materials can be useful.

In some embodiments, the same material can provide the gate electrode function and also provide a support function. For example, doped silicon can function as the gate electrode and support the OFET.

Gate Dielectric

The gate dielectric is provided on the gate electrode to electrically insulate the gate electrode from the balance of the OFET device. The gate dielectric can be provided in the OFET as a separate layer, or formed on the gate such as by oxidizing the gate material to form the gate dielectric. The dielectric layer can comprise two or more layers having different dielectric constants.

The gate dielectric should have a suitable dielectric constant that can vary widely depending on the particular device and circumstance of use. For example, a dielectric constant from about 2 to about 100 or even higher is known for a gate dielectric. The gate dielectric layer should have a resistivity of $10^{14}$ ohm-cm or greater in OFET applications. The gate dielectric can comprise organic polymeric materials, inorganic materials, and organic-inorganic composite materials. Useful polymer materials for the gate dielectric can comprise one or more dielectric polymers such as acrylic and styrenic polymers selected from the group consisting of: acrylic, styrenic and styrenic-acrylic latexes, solution-based acrylic, styrenic and styrenic-acrylic polymers, and combinations thereof heteroatom-substituted styrenic polymers selected from the group consisting of: partially hydrogenated poly(4-hydroxy)styrene, poly(4-hydroxy)styrene, and copolymers of poly(4-hydroxy)styrene with hydroxyethyl(meth)acrylate, alkyl(meth)acrylate, styrene, and alkyl-substituted styrene wherein the alkyl group is a $C_1$ to $C_{18}$ straight or branched chain alkyl group, phenol-aldehyde (co)polymers and (co) oligomers and combinations thereof. The gate dielectric can comprise a polymeric material, such as poly(vinylidene difluoride) (PVDF), cyanocelluloses, polyimides, and others known in the art. The gate electric can comprise a plurality of layers of different materials having different dielectric constants.

In certain embodiments, polymer gate dielectric can possess one or more of the following characteristics: coatable out of solution, crosslinkable, photo-patternable, high thermal stability (for example, stable up to a temperature of about 250° C.), low processing temperatures (for example, less than about 150° C. or less than 100° C.), and are compatible with flexible substrates. Crosslinkable or photo-patternable polymers are particularly desirable. This is because they provide flexibility in manufacturing methods, would easily integrate with solution processed device layers, and could allow for high-speed roll-to-roll processing. Polymers are photo-patternable if they include one or more crosslinking (that is, crosslinkable) groups that can be induced to form a crosslinked network upon exposure to radiation (most commonly, UV radiation). The exposed (crosslinked portion of the polymer) becomes insoluble in certain solvents and the unexposed portion of the polymer can be washed away using a developing solvent. This is an example of a negative-acting photo-patternable polymer. It is also possible to photo-pattern a polymer that is initially insoluble in certain solvents and that becomes soluble in UV-exposed areas upon exposure. This is an example of a positive-acting photo-patternable polymer.

For OFET's, the polymeric dielectric layer generally has a thickness of less than about 5000 Angstroms (Å), typically less than about 3000 Å, or less than about 2000 Å. The polymeric dielectric layer generally has a thickness of at least about 500 Å or typically at least about 1000 Å. The thickness can be determined through known methods such as ellipsometry and profilometry. For embedded capacitors and printed circuit board applications, the thickness can include those described above for OFET's, but can also be at least 10 µm or at least 20 µm.

The term dielectric polymers herein encompasses homopolymers, copolymers derived from polymerization of two or more monomers, post-derivatized (co)polymers including graft (co)polymers, and low molecular weight homopolymers or copolymers. The polymers can be linear, branched, hyperbranched, or dendritic.

Useful materials for the gate dielectric can comprise, for example, an inorganic electrically insulating material. Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these materials can be used for the gate dielectric. In addition, polymeric materials such as polyimides and insulators that exhibit a high dielectric constant are also suitable dielectric materials as described in U.S. Pat. No. 5,981,970 (Dimitrakopoulous et al.).

Useful dielectric polymers include acrylic, styrenic, and styrenic-acrylic latexes comprising alkyl (meth)acrylate, styrene, and alkyl-substituted styrene wherein the alkyl group is a $C_1$ to $C_{18}$ straight or branched chain alkyl group. Useful optional monomers used to derive these latex-based polymers include (meth)acrylic acid, hydroxyethyl(meth)acrylate, and glycidyl(meth)acrylate. Such latexes are selected from the group: Latexes A, defined herein as one or more latex resins comprising at least 85 weight % or at least 90 weight % of alkyl (meth)acrylate, styrene, and alkyl-substituted styrene. Useful additional monomers used to derive these latex resins include (meth)acrylic acid (up to 5 weight %), hydroxyethyl (meth)acrylate (up to 10 weight %), and glycidyl(meth)acrylate (up to 5 weight %). Such latexes generally have an average particle size of less than about 150 nm or less than about 100 nm.

Particularly useful dielectric polymers with high resistivity (above $10^{14}$ ohm-cm) are Acrylic Latexes B and Styrene-Acrylic Latexes C and combinations thereof Acrylic Latexes B are defined herein as one or more acrylic latexes comprising at least 85 weight % or at least 90 weight % of methyl methacrylate or butyl acrylate or both. Styrene-Acrylic Latexes C are defined herein as one or more styrene-acrylic latexes comprising at least 85 weight % or at least 90 weight % of methyl methacrylate, butyl acrylate, or styrene, or mixtures thereof. Useful additional monomers used to derive Acrylic Latexes B and Styrene-Acrylic Latexes C include (meth)acrylic acid (up to 5 weight %), hydroxyethyl methacrylate (up to 10 weight %), and glycidyl methacrylate (up to 5 weight %). Commercial examples of acrylic and styrenic acrylic latexes useful as dielectric polymers include Joncryl® 95 and 1915 (co)polymers (Johnson Polymer). Methods for synthesizing suitable latex polymers have been reported in WO 03/099574 (Caspar et al.).

Further useful dielectric polymers include solution-based acrylic, styrenic and styrenic-acrylic polymers. Herein the term "solution-based" refers to materials that are soluble in solvents such as water or one or more common organic solvents including alcohols, ethers, esters, ketones, and aromatic hydrocarbons. Such solution-based acrylic, styrenic and styrenic-acrylic polymers have a Mw of less than 100,000 and an acid number less than about 250.

Useful dielectric polymers also include heteroatom-substituted styrenic polymers selected from the group consisting of: partially hydrogenated poly(4-hydroxy)styrene, poly(4-hydroxy)styrene (PHS), and copolymers of PHS with hydroxyethyl(meth)acrylate, alkyl(meth)acrylate, styrene, and alkyl-substituted styrene wherein the alkyl group is a $C_1$ to $C_{18}$ straight or branched chain alkyl group. When a PHS homopolymer is used, the branched structure is desired and the (co)polymers have an Mw of less than about 30,000. Partially hydrogenated PHS refers to PHS polymers that have been hydrogenated up to about 50 equivalent % of the unsaturation within the polymer. Commercial examples include PHS-B (branched PHS homopolymer; DuPont Electronic Technologies, Dallas, Tex.), Maruka Lyncur CMM (PHS copolymer with methyl methacrylate; Maruzen Petrochemical Co., LTD. Tokyo, Japan), Maruka Lyncur CHM (PHS copolymer with hydroxyethyl methacrylate; Maruzen), Maruka Lyncur CBA (PHS copolymer with butyl acrylate, Maruzen), Maruka Lyncur CST 15, 50, and 70 (PHS copolymers with styrene, Maruzen), and Maruka Lyncur PHM-C (partially hydrogenated PHS, Maruzen).

Other useful dielectric polymers include phenol-aldehyde (co)polymers/(co)oligomers and combinations thereof that are derived from mono- and bis-phenols and mono- and bis-aldehydes selected from the group consisting of: phenol, alkyl- and aryl-substituted phenols; formaldehyde, and alkyl-, aryl- and heteroatom-substituted aldehydes. The phenol-aldehyde resins can be further derivatized, for example, the hydroxy group converted to an ether group. Such (co) polymers/(co)oligomers have an Mw of 20,000 or less or 10,000 or less.

Other useful dielectric polymers include poly(vinyl acetate) homopolymers having an Mw of 100,000 or less.

The above polymers can be plasticized for improved flexibility, adhesion, compatibilization with an IR dye, among other characteristics. In certain instances, the plasticizer can be selected from the above classes of polymers. For example, a higher Tg or higher molecular weight (Mw) phenol-aldehyde polymer can be blended with a lower Tg or lower Mw phenol-aldehyde polymer. Another example is PHS blended with a phenol-aldehyde polymer. Examples of suitable plasticizers for some of the above classes of polymers comprise poly(ethylene) glycol, glycerol ethoxylate, di(ethylene glycol) dibenzoate, and phthalate-based plasticizers such as dibutyl phthalate. A number of potentially suitable plasticizers for various polymers and details regarding their use can be found in the following reference: "Handbook of Plasticizers," Ed. G. Wypych, ChemTec Publishing, Toronto, Ontario, 2004.

Source and Drain Electrodes

The source electrode and drain electrode are separated from the gate electrode by the gate dielectric while the organic semiconductor layer can be over or under the source electrode and drain electrode. The source and drain electrodes can be any useful electrically conductive material including but not limited to, those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof.

The thin film electrodes (for example, gate electrode, source electrode, and drain electrode) can be provided by any useful means such as physical vapor deposition (for example, thermal evaporation, sputtering) or ink jet printing. The patterning of these electrodes can be accomplished by known methods such as shadow masking, additive photolithography, subtractive photolithography, printing, microcontact printing, and pattern coating.

The organic semiconducting layer can be located over or under the source and drain electrodes, as described above in reference to the thin film transistor articles. Useful articles can also include an integrated circuit comprising a plurality of OFET's made by the process described herein. The n-channel organic semiconductor layer containing the above-described amic acid or amic ester of this invention is capable of being formed on any suitable substrate that can comprise the support and any intermediate layers such as a dielectric or insulator material, including those known in the art.

Processing

Organic semiconductor layers can be readily prepared by solution coating of an amic acid or amic ester of this invention and after coating solvent is removed, thermal dehydration imidization conversion of this compound in the coating to the corresponding arylene diimide compound in solid thin film form. The resulting organic semiconductor layer or the layer (s) of the gate dielectric can be deposited by spin coating. The entire process of making the thin film transistor devices or integrated circuits can be carried out below a maximum support temperature generally at or below 450° C. or typically at or below 250° C., or even at or below 200° C. The temperature selection generally depends on the nature of the amic acid or amic ester, support, and processing parameters known in the art, once a skilled artisan has the knowledge of the present invention contained herein. These temperatures are well below traditional integrated circuit and semiconductor processing temperatures that enable the use of any of a variety of relatively inexpensive supports, such as flexible polymeric supports. Furthermore, since the amic acid and amic esters are soluble in a number of solvents it affords flexibility in coating formulations and conditions. This enables production of relatively inexpensive integrated circuits containing organic thin film transistors using a significantly simplified process.

In cases where the gate dielectric is a polymer, both the organic semiconductor layer and the gate dielectric layer can be deposited from solution, making the coating of large areas less difficult. Furthermore, since the amic acid and ester of this invention are soluble in a number of solvents, further providing coating and manufacturing flexibility.

In one embodiment, an FET structure of FIG. 1a is prepared by spin coating the amic acid or amic ester precursor layer onto the dielectric layer with pre-patterned source and drain electrodes. In another embodiment, an FET structure of FIG. 1c is prepared by spin coating the amic acid or amic ester onto the substrate with pre-patterned source and drain electrodes. Heating the layer at appropriate temperature and time converts the amic acid or amic ester to obtain the corresponding semiconductive arylene diimide compound. Next, a dielectric layer in the form of a polymer is spin coated onto the organic semiconductor layer followed by the deposition of the gate electrode by vacuum deposition or liquid deposition of a conductive metal or metal dispersion, respectively. Thermal conversion of the amic acid or amic ester to the arylene diimide compound can be accomplished as describe above.

Devices in which the n-channel organic semiconductor layers described herein are useful include thin film transistors (TFT's), especially OFET's. Such layers can be used also in various types of devices having organic p-n junctions, such as the devices described on pages 13-15 of U.S. Patent Application Publication 2004/0021204 (Liu).

Electronic devices in which FET's and other devices are useful include, for example, more complex circuits such as shift registers, integrated circuits, logic circuits, smart cards, memory devices, radio-frequency identification tags, backplanes for active matrix displays, active-matrix displays (for example liquid crystal or OLED), solar cells comprising a multiplicity of thin-film transistors, ring oscillators, and complementary circuits, such as inverter circuits, for example, in combination with other transistors made using available p-type organic semiconductor materials such as pentacene. In an active matrix display, a thin film transistor device can be used as part of voltage hold circuitry of a pixel of the display. In devices containing FET's, the FET's are operatively connected in ways that are known in the art. In some embodiments, the multiplicity of the thin-film transistors is on a non-participating support that is optionally flexible.

The present invention provides at least the following embodiments and combinations thereof:

1. An organic composition that comprises an amic acid or amic ester.

2. The composition of embodiment 1 wherein the amic acid or amic ester is an arylene tetracarboxylic acid or ester precursor that is represented by the following Structure (I):

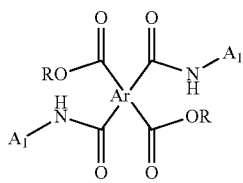

(I)

wherein Ar is an anthracene, naphthalene, or perylene nucleus and the four carbonyl groups are attached directly to peri carbon atoms, $A_1$ is an aryl, heteroaryl, non-aromatic alkyl, alkylaryl, fluoroalkyl, cycloalkyl, or heterocyclyl group, and R is hydrogen or an alkyl or cycloalkyl group that is the same or different as that defined for $A_1$.

3. The composition of embodiment 2 wherein Ar is naphthalene or perylene, $Ar_1$ is an alkyl, fluoroalkyl, alkylphenyl, phenyl, or cycloalkyl group, and R is hydrogen or a methyl or ethyl group.

4. The composition of embodiment 1 wherein the amic acid or amic ester is an arylene tetracarboxylic acid or ester precursor that is represented by the following Structure (II):

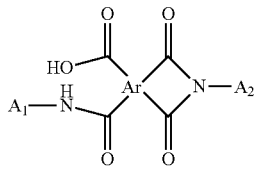

(II)

wherein Ar is an anthracene, naphthalene, or perylene nucleus and the four carbonyl groups are attached directly to peri carbon atoms, $A_1$ and $A_2$ are independently aryl, heteroaryl, non-aromatic alkyl, alkylaryl, fluoroalkyl, cycloalkyl, or heterocyclyl groups, and R is hydrogen or an alkyl or cycloalkyl group that is the same or different as that defined for $A_1$ and $A_2$.

5. The composition of embodiment 4 wherein Ar is naphthalene or perylene, and $A_1$ and $A_2$ are independently alkyl, fluoroalkyl, alkylphenyl, phenyl, or cycloalkyl groups, and R is hydrogen or a methyl or ethyl group.

6. The composition of embodiment 1 wherein the amic acid or amic ester is an arylene tetracarboxylic acid or ester precursor that is represented by the following Structure (III):

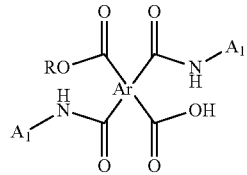

(III)

wherein Ar is an anthracene, naphthalene, or perylene nucleus and the four carbonyl groups are attached directly to peri carbon atoms, and $A_1$ is an aryl, heteroaryl, non-aromatic alkyl, alkylaryl, fluoroalkyl, cycloalkyl, or heterocyclyl group, and R is hydrogen or an alkyl or cycloalkyl group that is the same or different as that defined for $A_1$.

7. The composition of embodiment 6 wherein Ar is naphthalene or perylene, and $A_1$ is an alkyl, fluoroalkyl, alkylphenyl, phenyl, or cycloalkyl groups, and R is hydrogen or a methyl or ethyl group.

8. The composition of any of embodiments 1 to 7 including one or more organic solvents in which the amic acid or amic ester is soluble or dispersible.

9. The composition of any of embodiments 1 to 8 wherein the amic acid or amic ester is present in an amount of at least 0.5 and up to and including 10 weight % based on total composition weight.

10. The composition of any of embodiments 1 to 9 that consists essentially of the amic acid or amic ester.

11. The composition of any of embodiments 1 to 7 that consists only of the amic acid or amic ester.

12. The composition of any of embodiments 1 to 11 wherein the amic acid or amic ester is one of compounds I-1 through I-50:

I-1

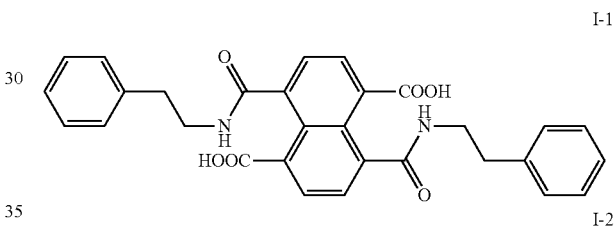

I-2

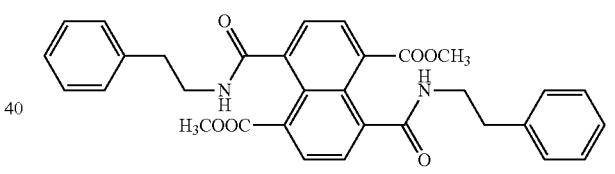

I-3

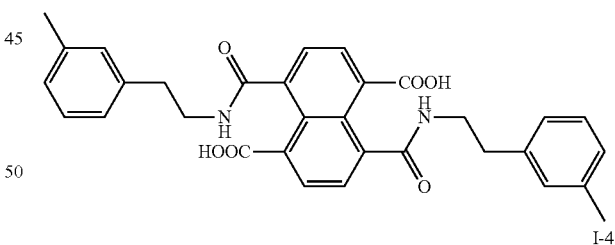

I-4

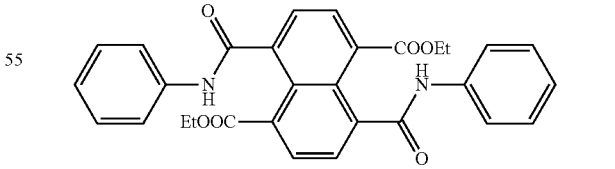

I-5

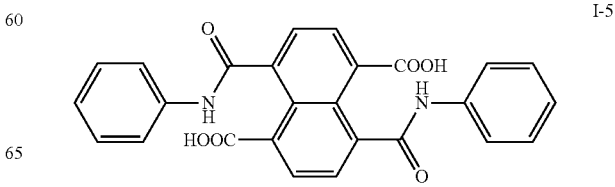

I-6
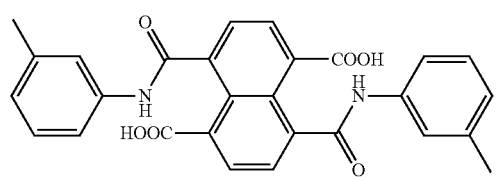
I-7
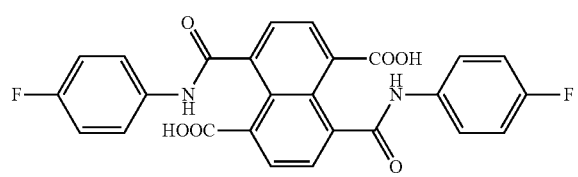
I-8
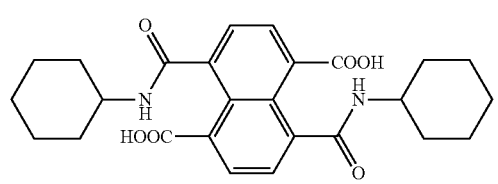
I-9
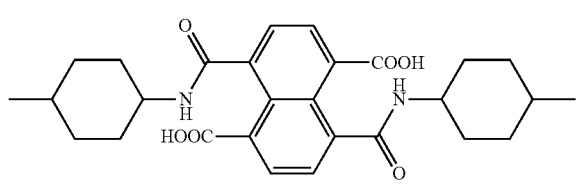
I-10
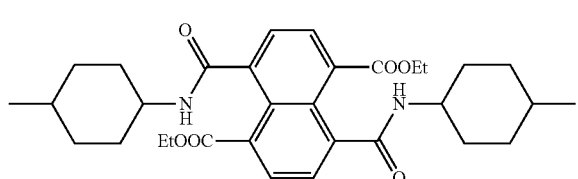
I-11
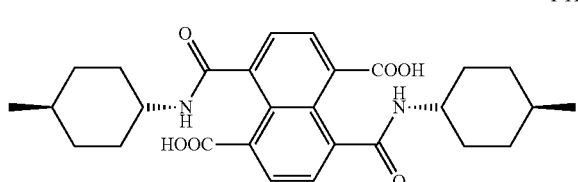
I-12
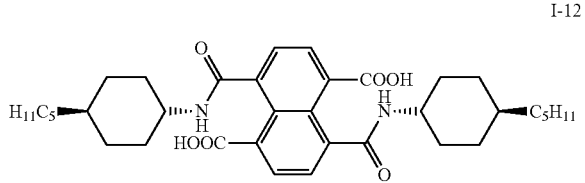
I-13
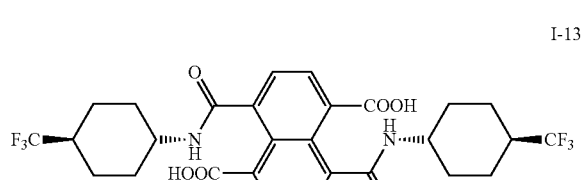
I-14
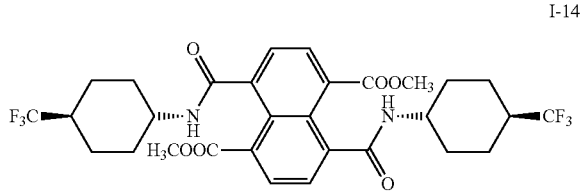
I-15
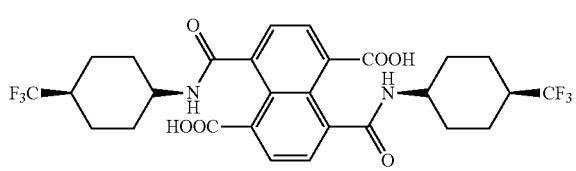
I-16
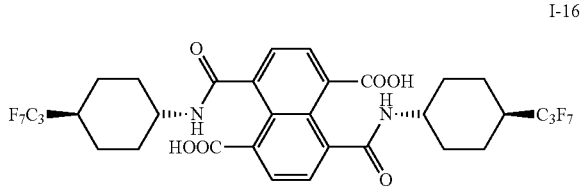
I-17
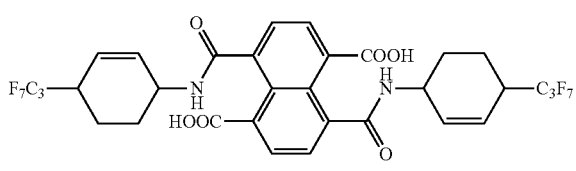
I-18
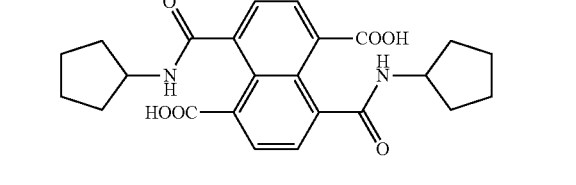
I-19
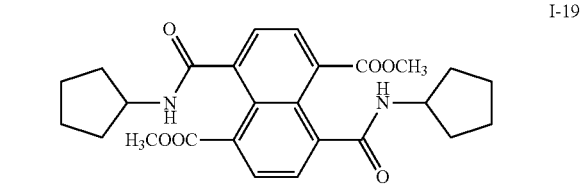
I-20
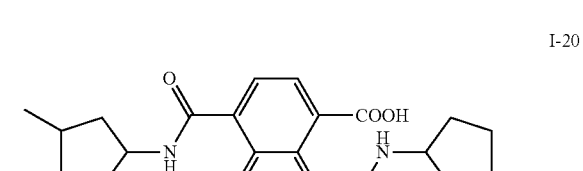
I-21
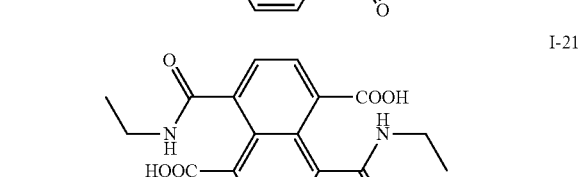

I-22
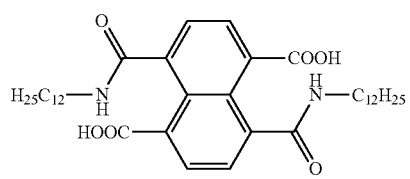
I-23
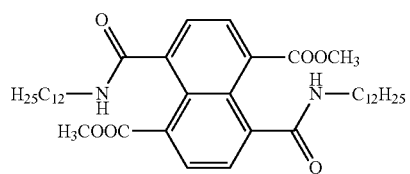
I-24
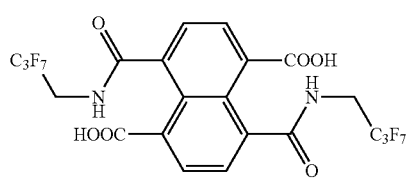
I-25
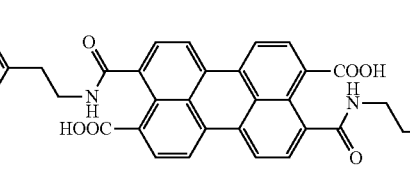
I-26
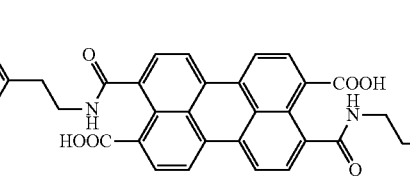
I-27
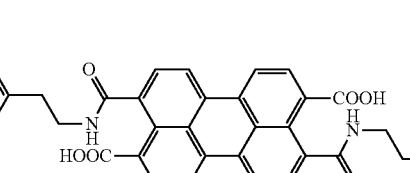
I-28
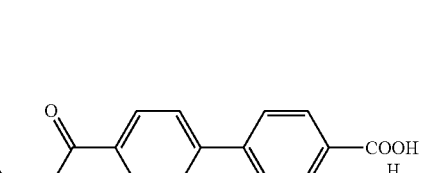
I-29
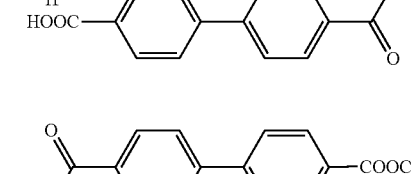
I-30
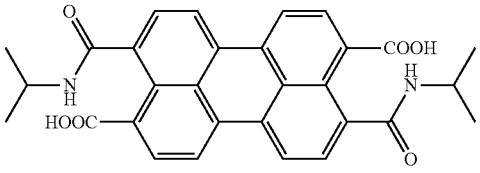
I-31
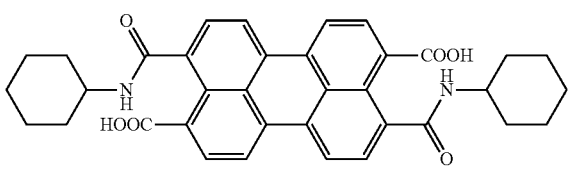
I-32
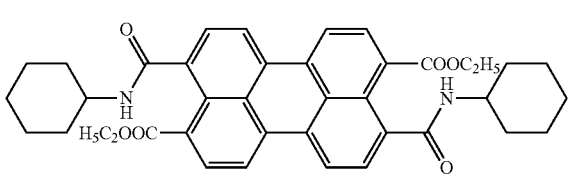
I-33
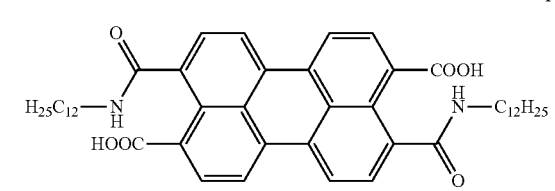
I-34
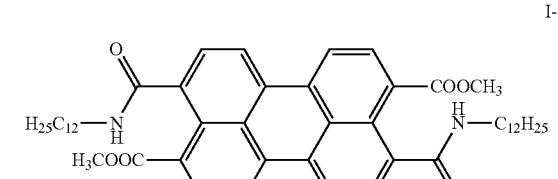
I-35
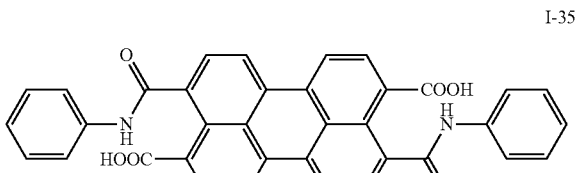
I-36
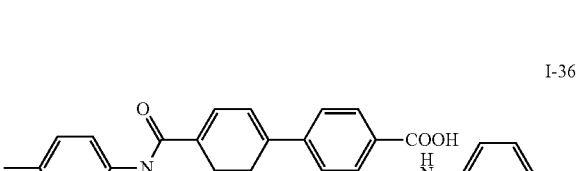
I-37
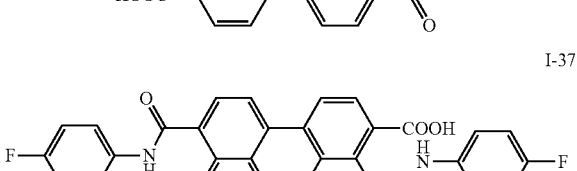

I-38
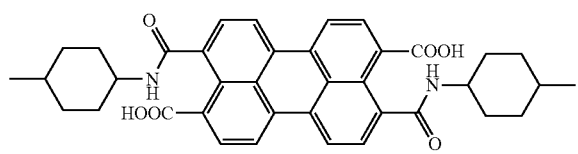
I-39
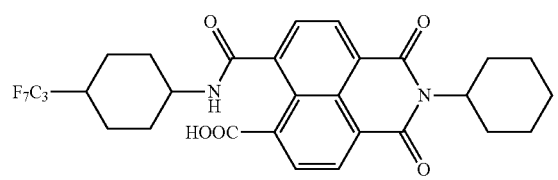
I-40
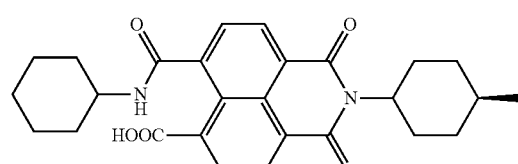
I-41
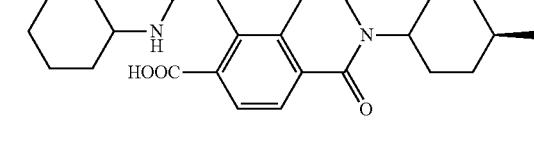
I-42
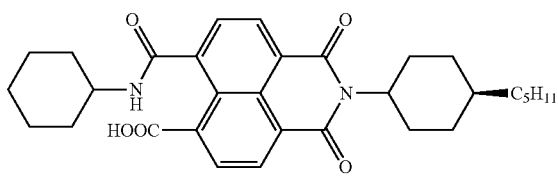
I-43
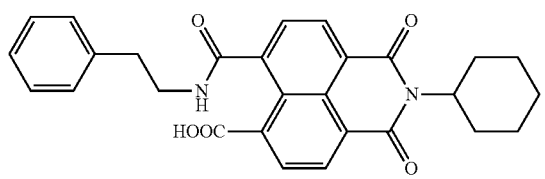
I-44
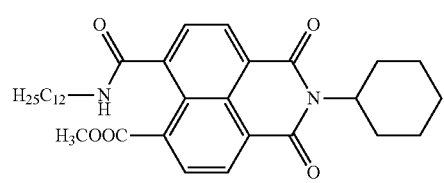
I-45
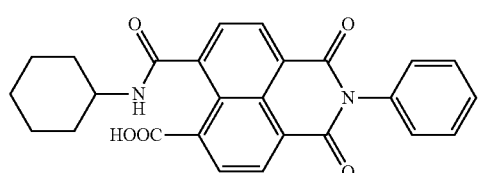
I-46
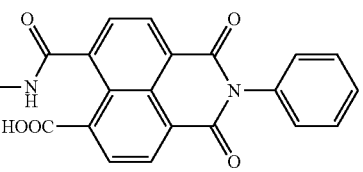
I-47
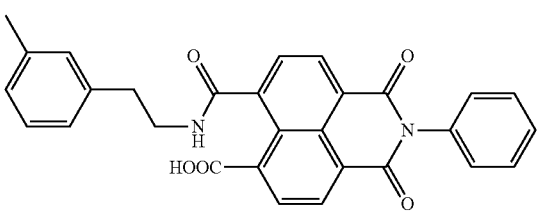
I-48
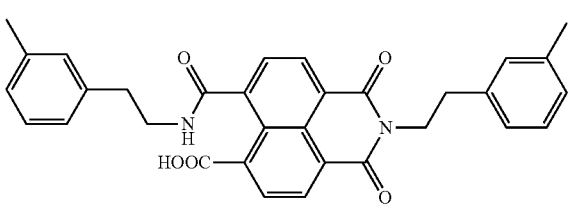
I-49
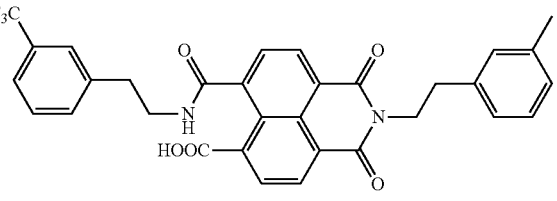
I-50
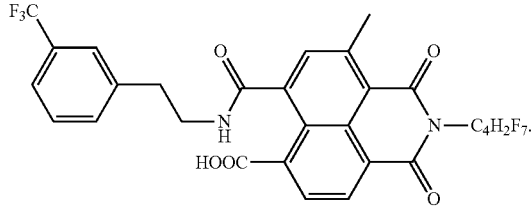
13. An arylene tetracarboxylic acid or ester that is represented by the following Structure (I), (II), or (III):
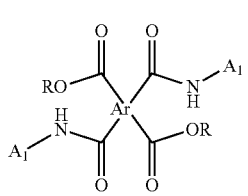
(I)
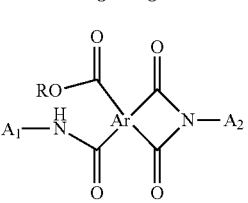
(II)

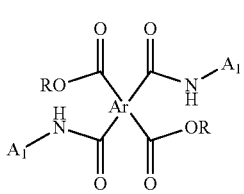
(III)

wherein Ar is an anthracene, naphthalene, or perylene nucleus and the four carbonyl groups are attached directly to peri carbon atoms, $A_1$ and $A_2$ are independently aryl, heteroaryl, non-aromatic alkyl, alkylaryl, fluoroalkyl, cycloalkyl, or heterocyclyl groups, and R is hydrogen or an alkyl or cycloalkyl group that is the same or different as that defined for $A_1$ and $A_2$.

14. The arylene tetracarboxylic acid or ester of embodiment 13 wherein Ar is naphthalene or perylene, $Ar_1$ is an alkyl, fluoroalkyl, alkylphenyl, phenyl, or cycloalkyl group, and R is hydrogen or a methyl or ethyl group.

The present invention is demonstrated by the following examples that are intended to be exemplary and not limiting in any manner.

INVENTION EXAMPLE 1

Preparation of 1,5-Naphthalenedicarboxylic acid-4,8-bis[(dodecylamino)-carbonyl] (Compound I-22)

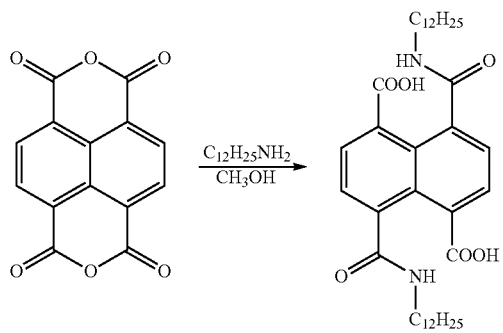

Freshly sublimed 1,4,5,8 naphthalene tetracarboxylic acid dianhydride (46 mg) was added to methanol (4 ml) and sonicated for 5 minutes to form a cloudy dispersion. Dodecylamine (67 mg) was added to the dispersion and sonicated to obtain a clear pale yellow solution. 1H NMR and IR spectra of the product were consistent with assigned structure. $^1$H NMR (CD$_3$OD, 300 MHz): δ(ppm)=7.91 (m, 4H, J=~7 Hz), 2.84 (dd, 4H, J=7.3 Hz), 1.59 (broad m, 4H), 1.6 (be. m., 36H), 0.90 (m, 6H); 13C (CD$_3$OD, 300 MHz): δ=169.77, 169.54, 134.62, 132.58, 128.90, 128.43, 127.44, 39.53, 31.91, 29.59, 29.48, 29.34, 29.31, 29.05, 27.37, 26.30, 22.57.

Conversion of 1,5-Naphthalenedicarboxylic acid-4,8-bis[(dodecylamino)-carbonyl] to N,N'-bis(dodecyl)naphthalene diimide in Solid State

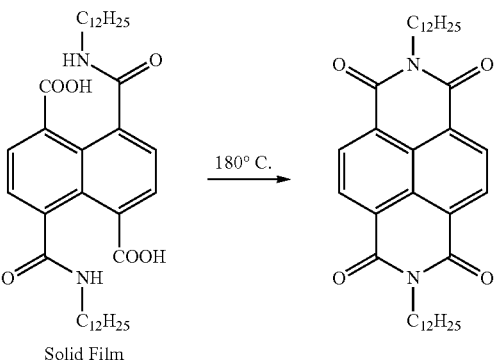

Solid Film

Figure 2D:
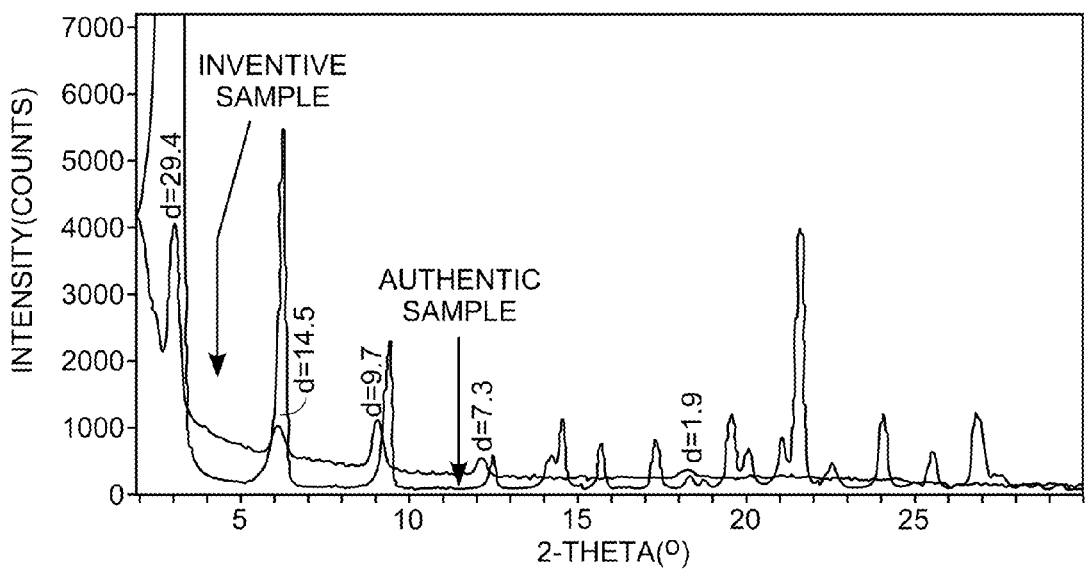
Figure 2B:
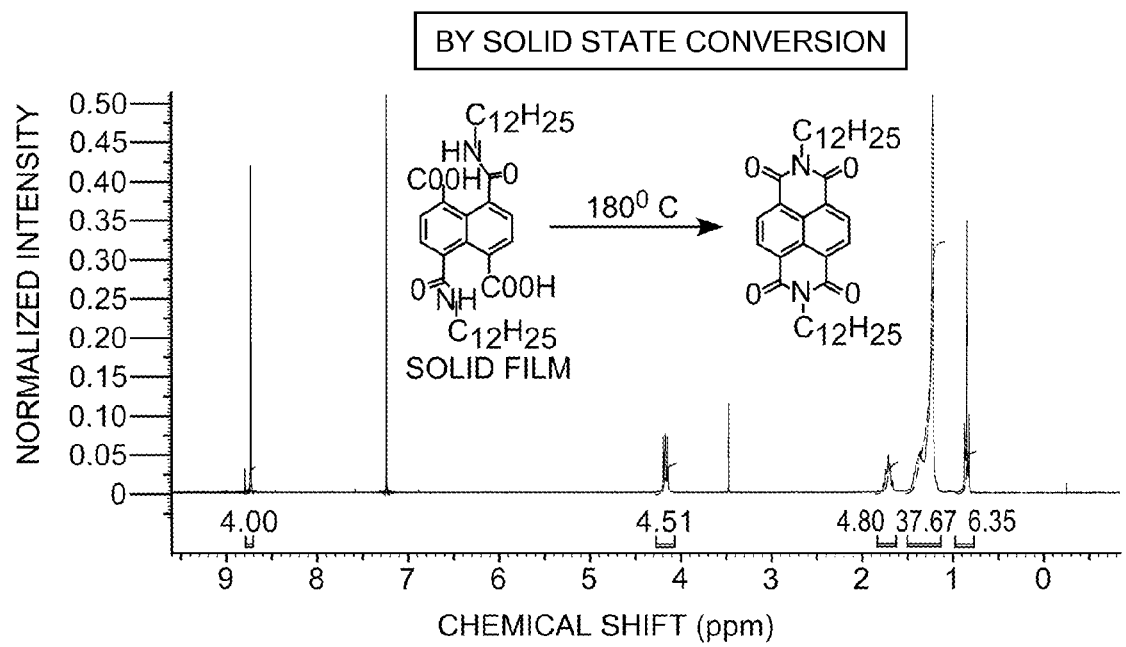
Figure 2C:
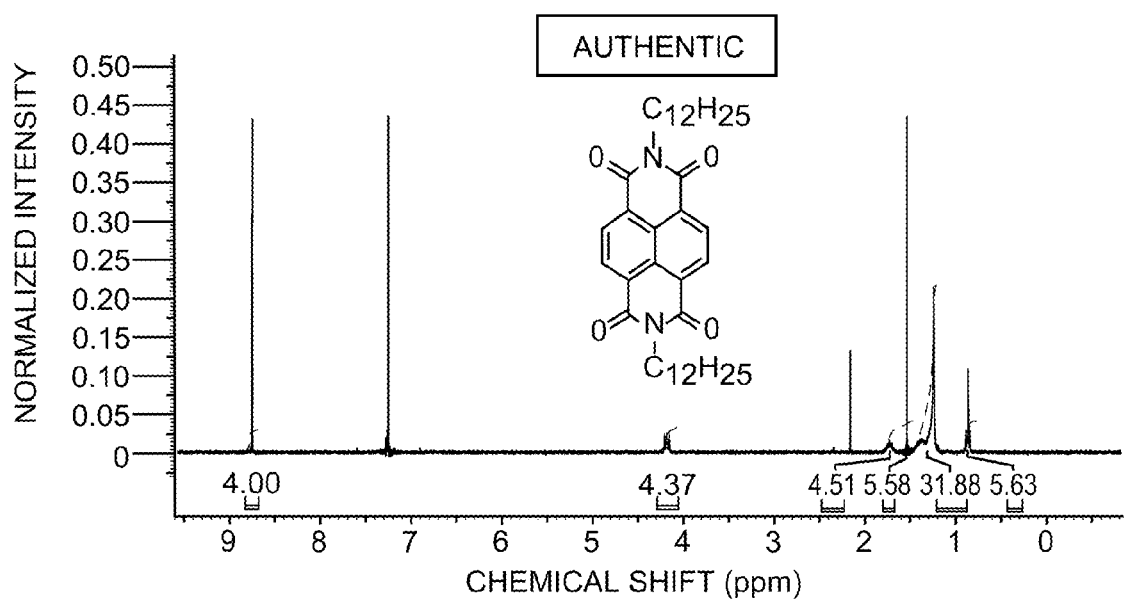

A 2 wt. % solution of 1,5-naphthalenedicarboxylic acid-4, 8-bis[(dodecylamino)carbonyl] in dimethylacetamide was drop cast onto a glass plate and solvent evaporated to form an article with the coated amic acid precursor. Absorption spectrum was recorded and the plate was heated at 180° C. for 20 minutes. Absorption spectrum after heating clearly shows the transformation of the starting material to the product semiconductive arylene diimide compound forming a semiconductor layer in the article. FIG. 2A shows absorption spectrum before and after heating and comparison of the product spectrum with the absorption spectrum of the authentic sample. Furthermore, the thin film formed on the glass plate was extracted with CDCl$_3$ and $^1$H NMR was recorded and compared with that of an authentic sample. FIG. 2B shows $^1$H NMR spectra of N,N'-bis(dodecyl)naphthalene diimide prepared by thermal conversion of the amic acid precursor, 5-naphthalenedicarboxylic acid-4,8-bis[(dodecylamino)carbonyl] in solid state and comparison with that of an authentic sample is shown in FIG. 2C. To confirm the purity of the material the X-ray powder diffraction of the material made by solid state conversion was compared with an authentic sample (see FIG. 2D).

This example clearly demonstrates that an amic acid of this invention can be cleanly converted to the corresponding arylene diimide in solid state by a thermal dehydration imidization reaction to provide an article with a semiconductor layer. The chemical identity of the final product (arylene diimide) obtained in solid thin film was established by $^1$H NMR and X-ray diffraction. It was shown that the method described herein generated arylene diimides cleanly and in high purity from the solvent soluble amic acid or esters of this invention.

INVENTION EXAMPLE 2

Preparation of 1,5-Naphthalenedicarboxylic acid-4,8-bis[(phenylethylamino)-carbonyl] (Compound I-1)

Conversion of 1,5-Naphthalenedicarboxylic acid-4,8-bis[(phenylethylamino)-carbonyl] to N,N'-bis(phenylethyl)naphthalene diimide in Solid State

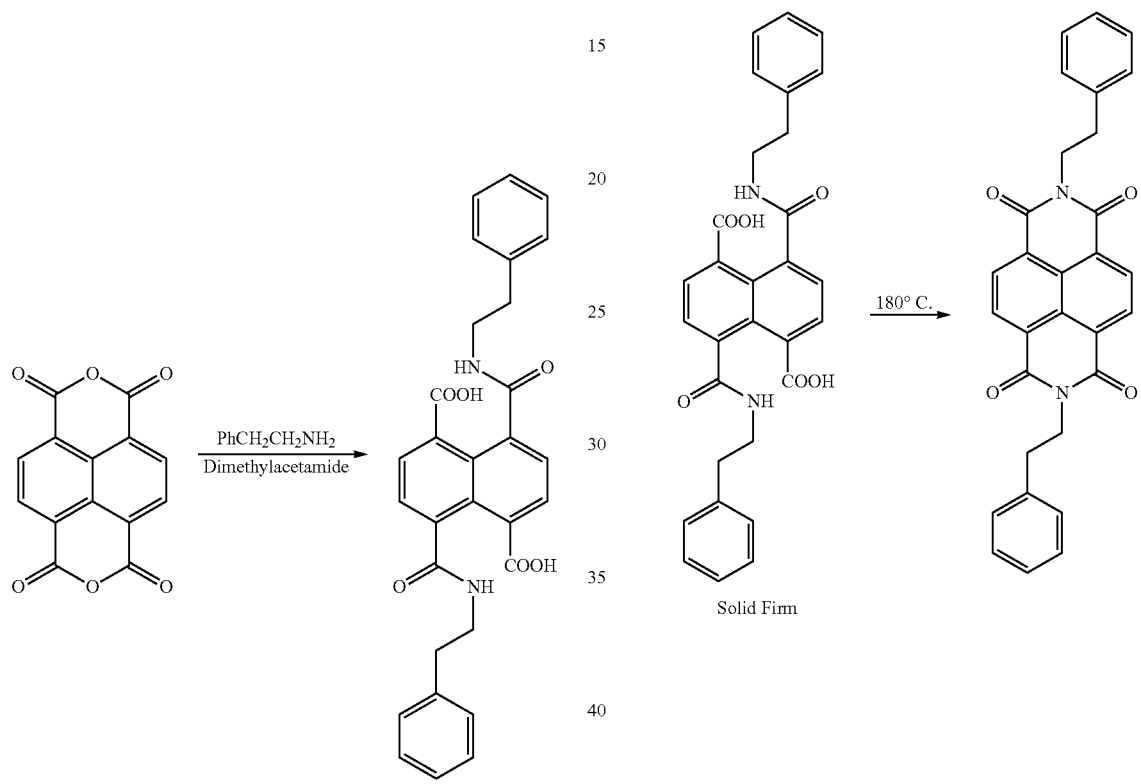

To a stirred dispersion of freshly sublimed 1,4,5,8-naphthalene tetracarboxylic acid dianhydride (46 mg, 0.17 mmol) in dimethylacetamide (4 ml), a solution of phenylethylamine (41 mg, 0.34 mmol) in dimethylacetamide (1 ml) was added dropwise to obtain a clear pale yellow solution. Solvent was removed under reduced pressure to obtain an oily solid. $^1$H and $^{13}$C NMR spectra of the product were consistent with assigned structure. $^1$H NMR (CD$_3$OD, 300 MHz): δ(ppm) =7.98-7.82 (dd, 4H, J=~7 Hz), 7.39-7.15 (m, 10H), 3.59 (q, 2H, J=~7 Hz), 3.15-3.04 (m, 4H), 2.96-2.84 (m, 4H); $^{13}$C (CD$_3$OD, 300 MHz): δ=162.92, 136.46, 131.23, 129.21, 128.81, 126.95, 126.89, 126.84, 42.43, 34.43.

A 2 wt. % solution of 1,5-naphthalenedicarboxylic acid-4, 8-bis[(phenylethylamino)carbonyl] in dimethylacetamide was drop cast onto a glass plate and solvent evaporated to form an article with the coated amic acid. Absorption spectrum was recorded and the plate was heated at 180° C. for 20 minutes. The absorption spectrum after heating clearly showed the transformation of the starting material to the product semiconductive arylene diimide compound, forming a semiconductor layer in the article. Furthermore, the thin film formed on the glass plate was extracted with CDCl$_3$ and $^1$H NMR was recorded and compared with that of an authentic sample. $^1$H NMR (CDCl$_3$, 300 MHz): δ(ppm)=8.83 (s, 4H), 7.4-7.1 (m, 10H), 4.35 (m, 4H), 3.04 (m, 4H), $^{13}$C (CD$_3$OD, 300 MHz): δ=162.92, 136.46, 131.23, 129.21, 128.81, 126.95, 126.89, 126.84, 42.43, 34.43.

This example clearly demonstrates that an amic acid of this invention can be cleanly converted to the corresponding arylene diimide in solid state by a thermal dehydration imidization reaction to provide an article with a semiconductor layer. The chemical identity of the final product (arylene diimide) obtained in solid thin film was established by $^1$H NMR. It was shown that the method described herein generated arylene diimides cleanly and in high purity from the solvent soluble amic acid and amic esters of this invention.

INVENTION EXAMPLE 3

Preparation of 1,5-naphthalenedicarboxylic acid-4,8-bis[(cyclopentylamino)carbonyl] (Compound I-18)

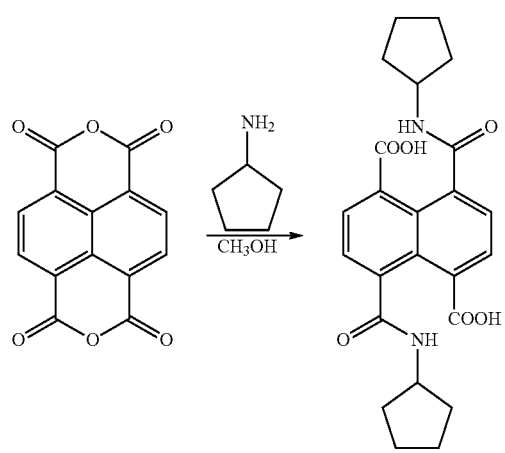

Freshly sublimed 1,4,5,8-napthalene tetracarboxylic acid dianhydride (44 mg) was added to methanol (2 ml) and sonicated for 5 minutes to form a cloudy dispersion. Dodecylamine (30 mg) was added to the dispersion that was again sonicated to obtain a clear pale yellow solution. $^1$H NMR and IR spectra of the product were consistent with assigned structure. $^1$H NMR (CD$_3$OD, 300 MHz): δ(ppm)=7.91 (d, 2H, J=~7 Hz), 7.36 (d, 2H, J=~7 Hz), 3.49 (q, 2H, J=~7 Hz), 2.1-1.45 (m, 16H), 13C (CD$_3$OD, 300 MHz): δ=169.81, 169.58, 134.6, 132.54, 128.92, 127.49, 34.8, 30.81, 23.67.

Conversion of 1,5-naphthalenedicarboxylic acid-4,8-bis[(cyclopentylamino)carbonyl] to N,N'-bis(cyclopentyl)naphthalene diimide in Solid State

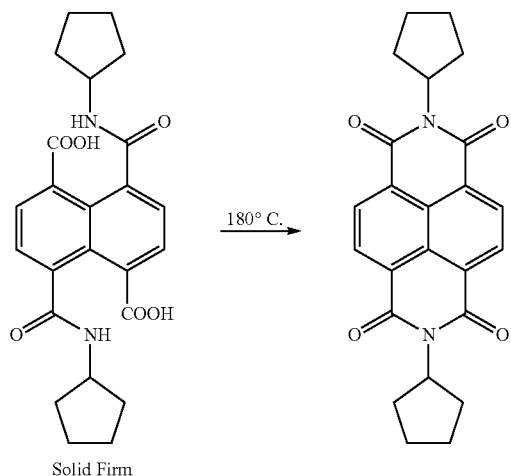

Figure 3A:
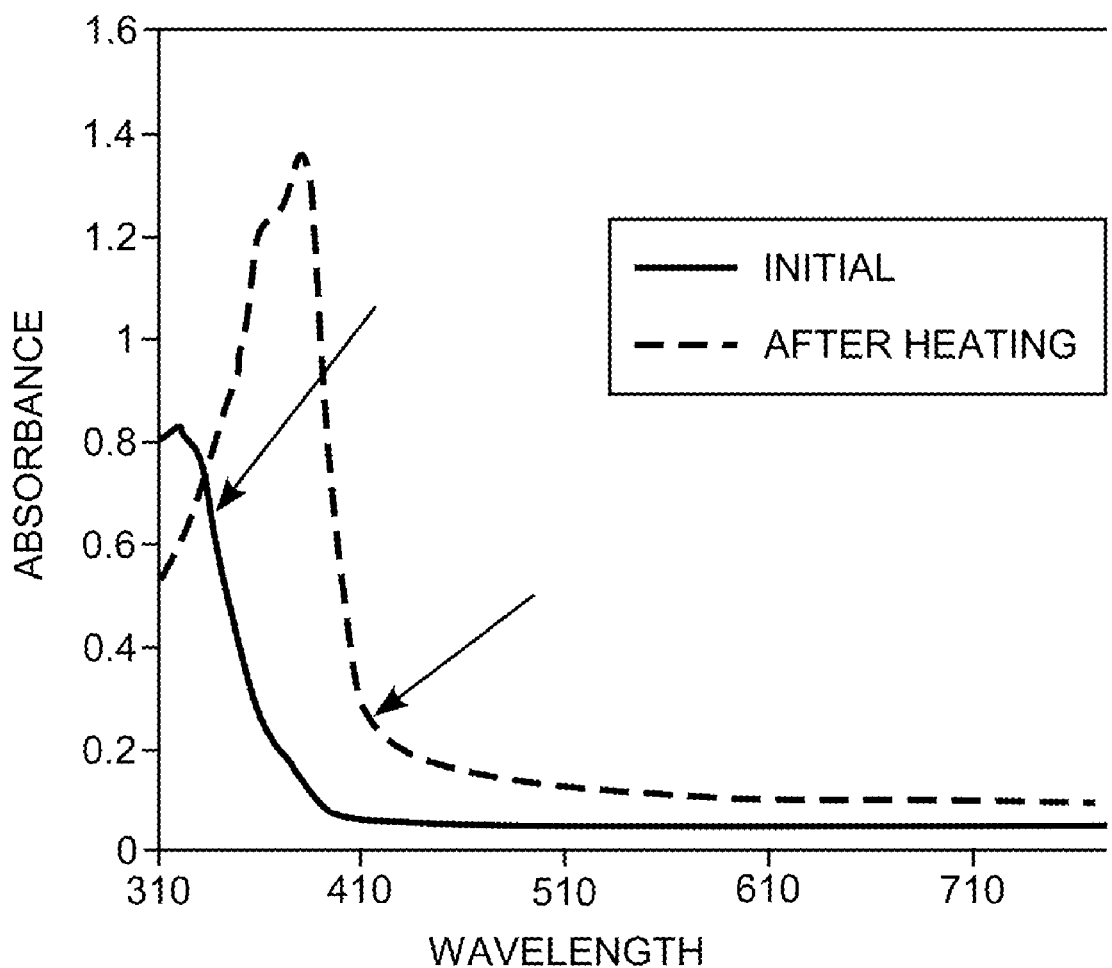
FIGS. 3A, 3B, and 3C are graphical plots that provide analytical characterizations used in Invention Example 3 below.
Figure 3B:
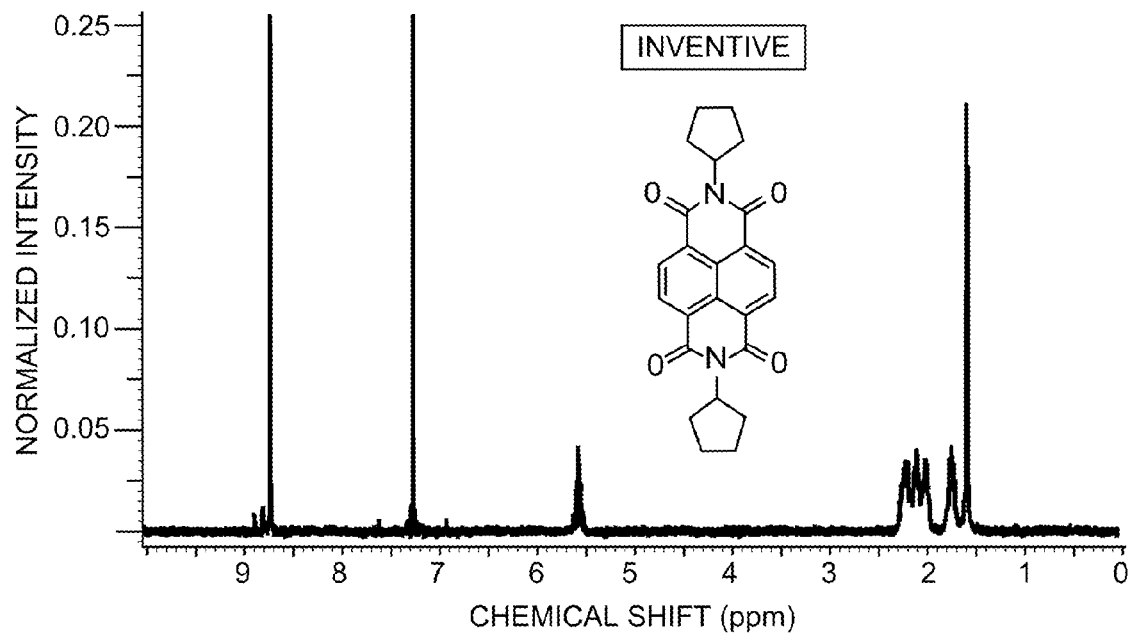
Figure 3C:
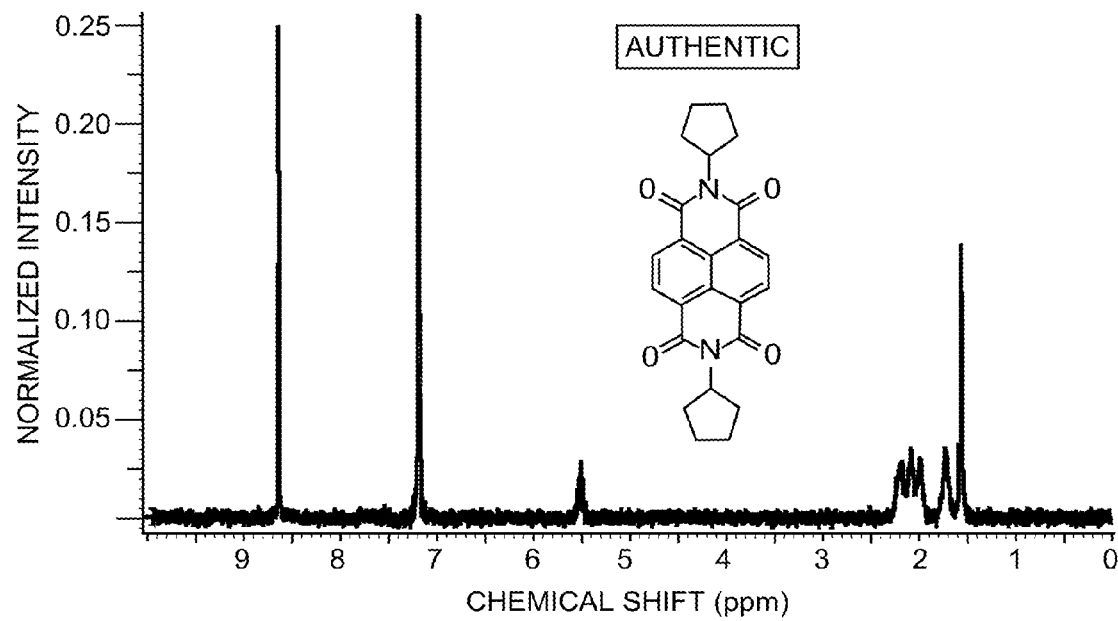

A 2 wt. % solution of 1,5-naphthalenedicarboxylic acid-4,8-bis[(cyclopentyl)carbonyl] was spin coated onto a glass plate at 800 RPM to form an article coated with an amic acid precursor. The glass plate was heated on a hot plate at 70° C. to remove any excess solvent. A UV-Vis spectrum was recorded from 310 nm-800 nm. The article was then heated to 180° C. for 10 minutes and an absorption spectrum showed characteristic absorption bands of N,N'-bis(cyclopentyl) naphthalene diimide (see FIG. 3A). Furthermore, the arylene diimide formed in the article was extracted with CDCl$_3$ and a $^1$H NMR spectrum was recorded and compared with that of an authentic sample. FIG. 3B shows $^1$H NMR spectra of N,N'-bis(cyclopentyl)naphthalene diimide prepared by thermal conversion of 5-naphthalenedicarboxylic acid-4,8-bis [(cyclopentylamino)-carbonyl] in solid state and in comparison with that of authentic sample in FIG. 3B.

This example clearly demonstrates that the amic acid of this invention can be cleanly converted to the corresponding arylene diimide in solid state by a thermal dehydration imidization reaction. The chemical identity of the final semiconductive compound in the solid thin film was established by $^1$H NMR and X-ray diffraction and showed that the method described herein generates arylene diimides cleanly and in high purity from the corresponding solvent soluble amic acid of this invention.

INVENTION EXAMPLE 4

Preparation of Dimethyl 4,8-bis[cyclopentylcarbamoyl)naphthalene-1,5-dicarboxylate] (Compound I-19)

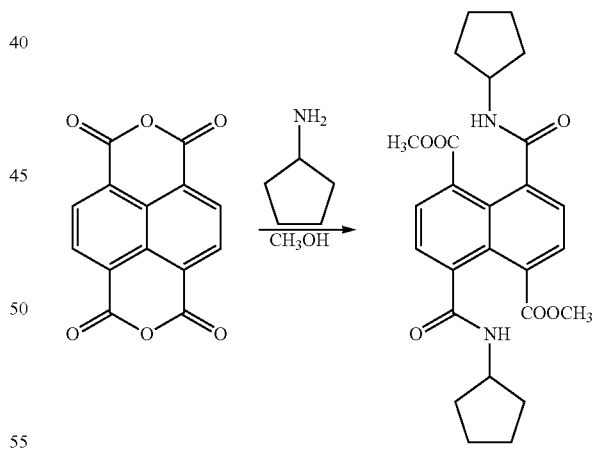

To a stirred dispersion of freshly sublimed 1,4,5,8 naphthalene tetracarboxylic acid dianhydride (46 mg, 0.17 mmol) in methanol (4 ml), a solution of cyclopentyl (30 mg, 0.34 mmol) in methanol (1 ml) was added dropwise. Solution was stirred for additional 30 minutes to obtain a clear pale yellow solution. Solvent was removed under reduced pressure to obtain a yellowish solid. $^1$H and $^{13}$C NMR spectra of the product were consistent with assigned structure. $^1$H NMR (CD$_3$OD, 300 MHz) δ=7.91 (d, 2H, J=~7 Hz), 7.36 (d, 2H, J=~7 Hz), 3.49 (q, 2H, J=~7 Hz), 3.9 (s, 6H); 2.1-1.45 (m, 16H); $^{13}$C (CD$_3$OD, 300 MHz): δ=169.81, 169.58, 132.54, 128.92, 127.49, 127.31, 126.42, 51.99, 30.81, 23.67.

Conversion of Dimethyl 4,8-bis[cyclopentylcarbamoyl)naphthalene-1,5-dicarboxylate] (Compound 1-19) to N,N'-bis(cyclopentyl)naphthalene diimide in Solid State

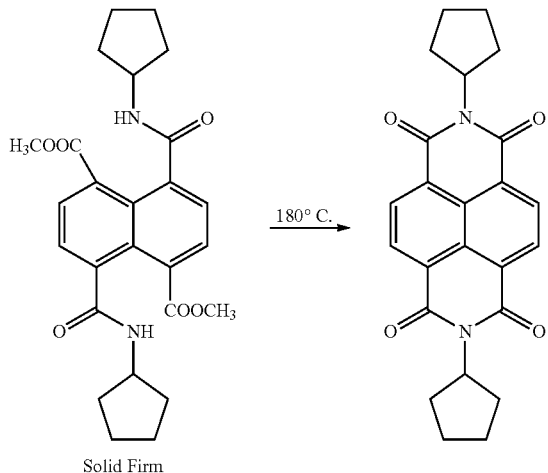

Solid Firm

A 2 wt. % solution of dimethyl 4,8-bis[cyclopentylcarbamoyl)-naphthalene-1,5-dicarboxylate] (Compound 1-18) was spin coated onto a glass plate at 800 RPM to form an article coated with an amic ester. The glass plate was heated on a hot plate at 180° C. for 15 minutes and the arylene diimide formed in the article was extracted with CDCl$_3$ and a $^1$H NMR spectrum was recorded and found to be identical to that of an authentic sample.

INVENTION EXAMPLE 5

Thin Film Device Preparation

OTFT Test Device Preparation Employing Arylene Diimide Generated in Thin Solid Film from Amic Acid Precursor In order to test the electrical characteristics of the semiconductive material, field-effect transistors were made using the top-contact geometry described above. The substrate was a heavily doped silicon wafer that also served as the gate electrode of the transistor. The gate dielectric was a thermally grown SiO$_2$ layer with a thickness of 190 nm. The wafer was cleaned for 10 minutes in a piranah solution, followed by a 6-minute exposure in a UV/ozone chamber. The cleaned surface was then treated with a self-assembled monolayer of octadecyltrichlorosilane (OTS), made from a heptane solution under a humidity-controlled environment. Water contact angles and layer thickness were measured to ensure the quality of the treated surface. Surfaces with a good quality OTS layer have water contact angles>90°, and a thickness determined from ellipsometry in the range of 27 Å to 35 Å.

A semiconductor layer of an arylene diimide was prepared by solid state thermal conversion of the corresponding amic acid of this invention. Accordingly, the OTS/SiO$_2$ wafer was placed on a hotplate set at 80° C. A composition of this invention that was a methanol solution of 1,5-naphthalenedicarboxylic acid-4,8-bis[(cyclopentylamino)carbonyl] (prepared in Invention Example 1) was diluted with 20 volume % chloroform and drop cast onto the wafer and smeared to make a more consistent coating of the amic acid precursor. The hotplate temperature was raised to 180° C. over a period of about 5 minutes and the wafer was then heated at 180° C. for 10 minutes in air. The resulting thin film of N,N'-bis(cyclopentyl)naphthalene diimide was used as a n-type semiconductor layer. The thickness of the layer was a variable in some experiments, but it was estimated to be 17-25 nm. OTFT devices using top source-drain contact configuration were made by depositing gold source drain contacts of thickness 60 nm through a shadow mask to provide thin film transistor devices. The channel width was held at 650 μm while the channel lengths were varied between 50 and 150 μm.

Device Measurement and Analysis:

Electrical characterization of the thin film transistor devices was performed using a Hewlett Packard HP 4145B® semiconductor parameter analyzer. The probe measurement station was held in a positive argon environment for all measurements with the exception of those purposely used to test the stability of the devices in air. For each experiment performed, between 4 and 12 individual devices were tested for each semiconductive material and the results were averaged. For each thin film transistor device, the drain current ($I_d$) was measured as a function of source-drain voltage ($V_d$) for various values of gate voltage ($V_g$). For most devices, $V_d$ was swept from 0 V to 100 V for each of the measured gate voltages, typically 0 V, 25 V, 75 V, and 100 V. In these measurements, the gate current ($I_g$) was also recorded in order to detect any leakage current through the device. Furthermore, for each thin film transistor device, the drain current was measured as a function of gate voltage for various values of source-drain voltage. For most devices, $V_g$ was swept from 0 V to 100 V for each of the drain voltages measured, typically 25 V, 75 V, and 100 V.

Parameters extracted from the data were field-effect mobility (μ), threshold voltage (Vth), sub-threshold slope (S), and the ratio of Ion/Ioff for the measured drain current. The field-effect mobility was extracted in the saturation region, where $V_d > V_g - V_{th}$. In this region, the drain current is given by the equation [see Sze in *Semiconductor Devices—Physics and Technology*, John Wiley & Sons (1981)]:

$$I_d = \frac{W}{2L}\mu C_{ox}(V_g - V_{th})^2$$

wherein W and L are the channel width and length, respectively, and $C_{ox}$ is the capacitance of the oxide layer, which is a function of oxide thickness and dielectric constant of the material. Given this equation, the saturation field-effect mobility was extracted from a straight-line fit to the linear portion of the $\sqrt{I_d}$ versus $V_g$ curve. The threshold voltage, $V_{th}$, is the x-intercept of this straight-line fit. Field-effect mobilities can also be extracted from the linear region, where $V_d \leq V_g - V_{th}$. Here, the drain current is given by the equation (see Sze in *Semiconductor Devices—Physics and Technology*, John Wiley & Sons (1981)):

$$I_d = \frac{W}{L}\mu C_{ox}\left[V_d(V_g - V_{th}) - \frac{V_d^2}{2}\right]$$

For these experiments, field-effect mobilities in the linear regime were not extracted, since this parameter is very much affected by any injection problems at the contacts. In general, non-linearity's in the curves of $I_d$ versus $V_d$ at low $V_d$ indicate that the performance of the thin film transistor device is limited by injection of charge by the contacts. In order to obtain results that are largely independent of contact imperfections of a given device, the saturation mobility rather than the linear mobility was extracted as the characteristic parameter of device performance.

The log of the drain current as a function of gate voltage was plotted. Parameters extracted from the log $I_d$ plot include the $I_{on}/I_{off}$ ratio and the sub-threshold slope (S). The $I_{on}/I_{off}$ ratio is simply the ratio of the maximum to minimum drain current, and S is the inverse of the slope of the $I_d$ curve in the region over which the drain current is increasing (that is, when the device is turning on).

Figure 4:
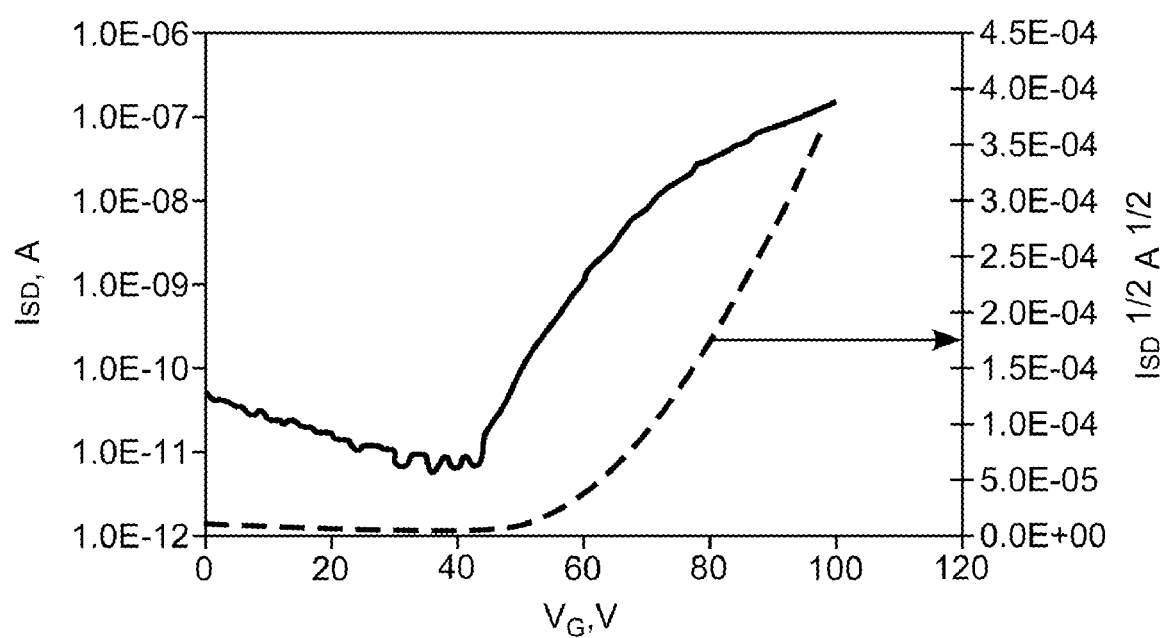
FIG. 4 is a graphical plot that provides data in Invention Example 5 below.

The thin film transistor devices were evaluated in an argon atmosphere using a Hewlett-Packard 4145B® semiconductor parameter analyzer. For each thin film transistor, the field effect mobility, µ, was calculated from the slope of the $(I_d)^{1/2}$ versus $V_g$ plot. FIG. 4 shows a plot of the square root of $I_d$ vs. $V_g$. A mobility of $10^{-3}$ cm$^2$/V·sec was calculated from this plot. The threshold voltage $V_T$ was 65 V and the current modulation, as can be seen from FIG. 4, between the on and the off state of the device, was about $10^4$.

This example clearly demonstrates that the arylene diimide prepared by thermal conversion of the amic acid prepared in Invention Example 1 performed well as n-type semiconductive material in a thin film transistor device.

INVENTION EXAMPLE 6

Preparation of 1,5-naphthalenedicarboxylic acid-4,8-bis[2-phenylethylamino)carbonyl]

Freshly sublimed 1,4,5,8-napthalene tetracarboxylic acid dianhydride (79 mg) was added to methanol (2 ml) and sonicated for 5 minutes to form a cloudy dispersion. Phenylethylamine (72.5 mg) was added to the dispersion that was again sonicated to obtain a clear pale yellow solution. $^1$H NMR and IR spectra of the product were consistent with assigned structure.

Conversion of 1,5-naphthalenedicarboxylic acid-4,8-bis[(phenylethylamino)carbonyl] to N,N'-bis(phenylethyl)naphthalene diimide in Solid State

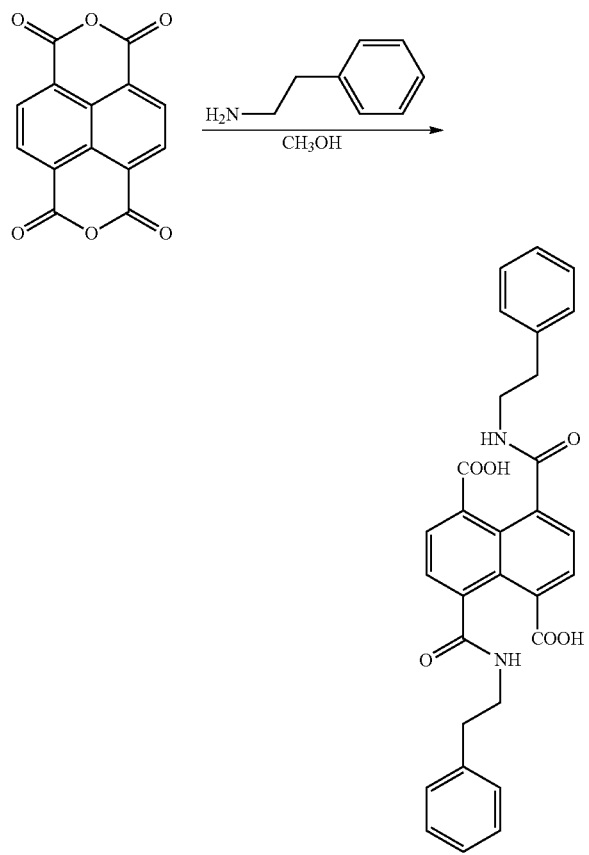

Figure 5A:
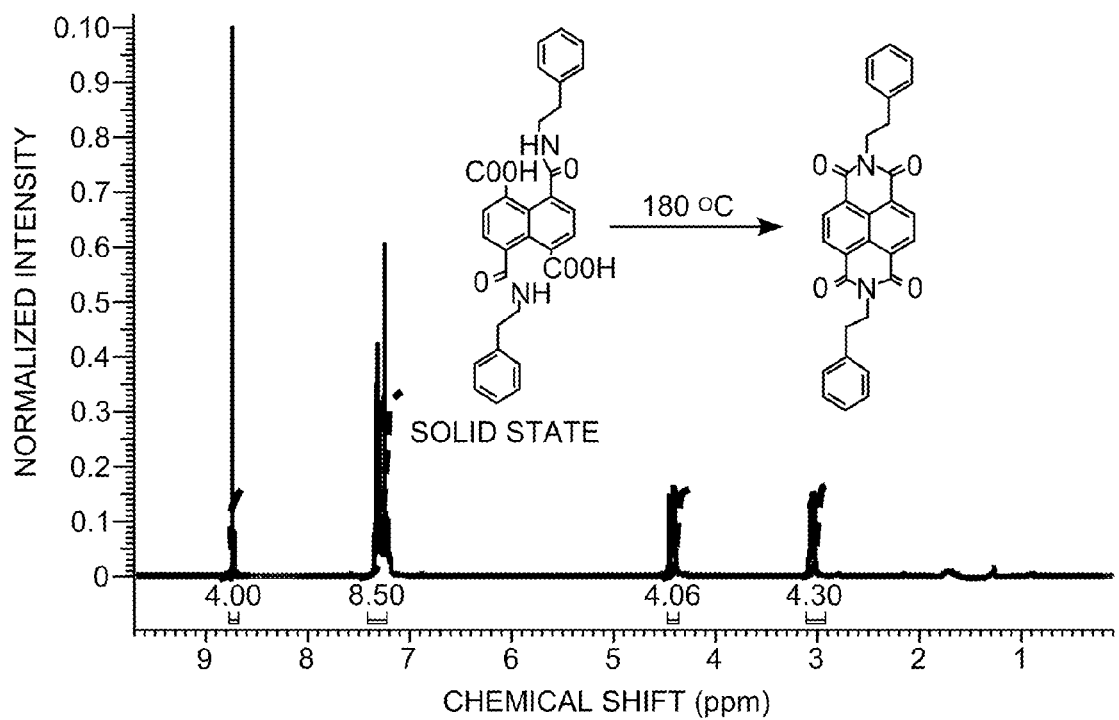
FIGS. 5A, 5B, and 6 are graphical plots that provide data in Invention Example 6 below.
Figure 5B:
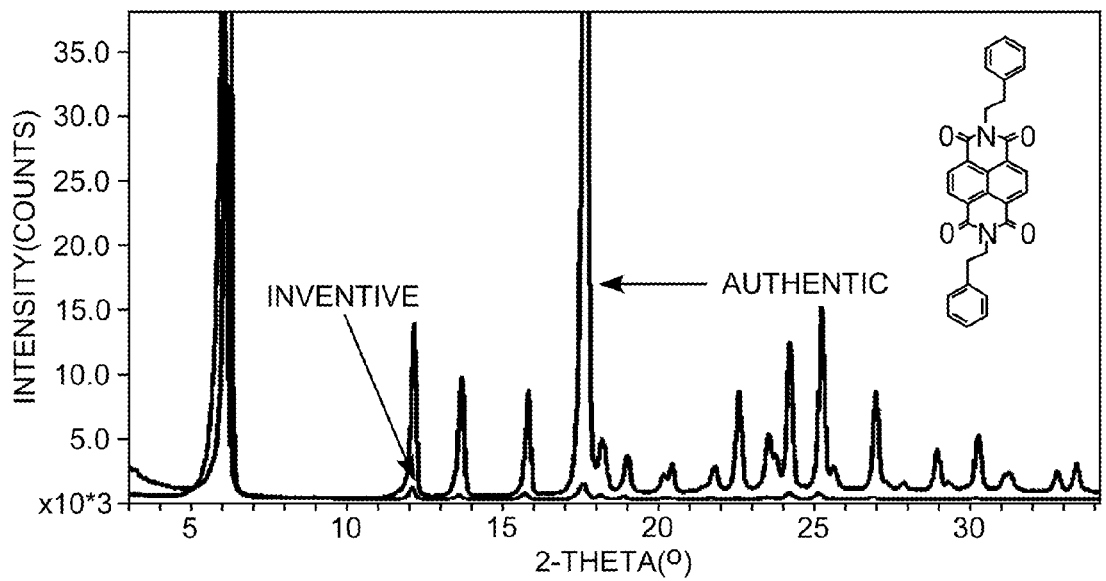

A solution of this invention consisting of 5-naphthalenedicarboxylic acid-4,8-bis[2-phenylethylamino)carbonyl] in methanol was drop cast onto a glass plate and heated to 180° C. for 10 minutes to form a coated article. The semiconductive layer formed on the glass plate was extracted with CDCl$_3$, filtered through a Whatman 0.45 µm glass microfiber syringeless filter, and a $^1$H NMR spectrum was consistent with the assigned structure (see FIG. 5A). X-ray powder diffraction of the resulting arylene diimide compound was compared with an authentic sample as shown in FIG. 5B.

This example clearly demonstrates that an amic acid of this invention can be cleanly converted to the corresponding arylene diimide in solid state by a thermal dehydration imidization reaction. The chemical identity of the final semiconductive material obtained in thin solid film was established by $^1$H NMR and X-ray diffraction that show that the method described herein generated an arylene diimide cleanly and in high purity from the corresponding solvent soluble amic acid.

Device Preparation:

OTFT Test Device Preparation Employing an Arylene Diimide Generated from an Amic Acid Precursor:

An OTS/SiO$_2$ wafer was placed on a hotplate set at 80° C. A methanol solution of 1,5-naphthalenedicarboxylic acid-4,8-bis[(phenylethyl-amino)carbonyl] was diluted with 20 volume % chloroform and drop cast onto the wafer and smeared to make a more consistent coating. The hot plate temperature was raised to 180° C. over a period of about 5 minutes and the wafer was heated at 180° C. for 10 minutes in air. The resulting thin film of N,N'-bis(phenylethyl)naphthalene diimide was used as a n-type semiconductor. The thickness of the semiconductor layer was a variable in some experiments, but was estimated to be 17-25 nm. OTFT devices using top source-drain contact configuration were made by depositing gold source drain contacts of thickness 60 nm through a shadow mask. The channel width was held at 650 μm while the channel lengths were varied between 50 and 150 μm.

Device Measurement and Analysis:

Electrical characterization of the devices prepared above was performed using a Hewlett Packard HP 4145B® semiconductor parameter analyzer. The probe measurement station was held in a positive argon environment for all measurements with the exception of those purposely used for testing the stability of the devices in air. For each experiment performed, between 4 and 12 individual devices were tested on each sample prepared, and the results were averaged. For each device, the drain current ($I_d$) was measured as a function of source-drain voltage ($V_d$) for various values of gate voltage ($V_g$). For most devices, $V_d$ was swept from 0 V to 100 V for each of the gate voltages measured, typically 0 V, 25 V, 75 V, and 100 V. In these measurements, the gate current ($I_g$) was also recorded in order to detect any leakage current through the device. Furthermore, for each device the drain current was measured as a function of gate voltage for various values of source-drain voltage. For most of the devices, Vg was swept from 0 V to 100 V for each of the drain voltages measured, typically 25 V, 75 V, and 100 V.

The log of the drain current as a function of gate voltage was plotted. Parameters extracted from the log $I_d$ plot included the $I_{on}/I_{off}$ ratio and the sub-threshold slope (S). The $I_{on}/I_{off}$ ratio is simply the ratio of the maximum to minimum drain current, and S is the inverse of the slope of the $I_d$ curve in the region over which the drain current is increasing (that is, when the device is turning on).

Figure 6:
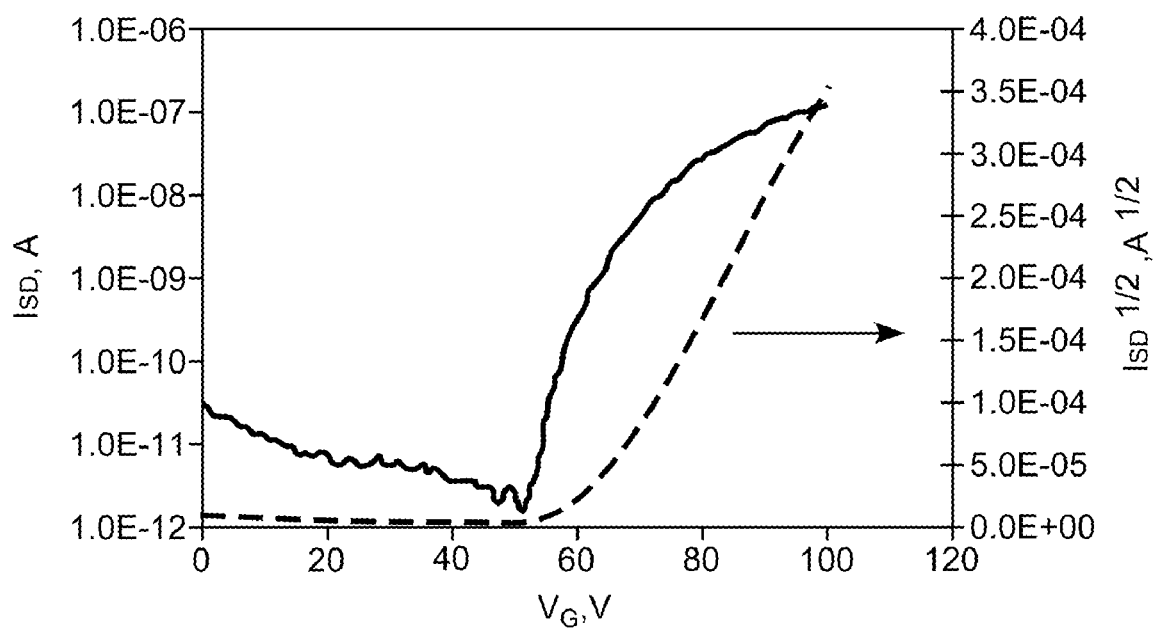

The thin film transistor devices were evaluated in an argon atmosphere using a Hewlett-Packard 4145B® semiconductor parameter analyzer. For each thin film transistor device, the field effect mobility (μ) was calculated from the slope of the $(I_d)^{1/2}$ versus $V_g$ plot (FIG. 6). This plot shows the square root of $I_d$ vs. $V_g$ and a mobility of $10^{-3}$ cm$^2$/V·sec was calculated from this plot. The threshold voltage $V_T$=63 V and current modulation, as can be seen from FIG. 6, between the on and the off state of the device was about $10^4$.

This example clearly demonstrates that the arylene diimide prepared from amic acid of this invention performed as n-type semiconductive material in a thin film transistor device.

INVENTION EXAMPLE 7

Preparation of 3,9-perylenedicarboxylic acid-4,10-bis[cyclopentylamino)-carbonyl]

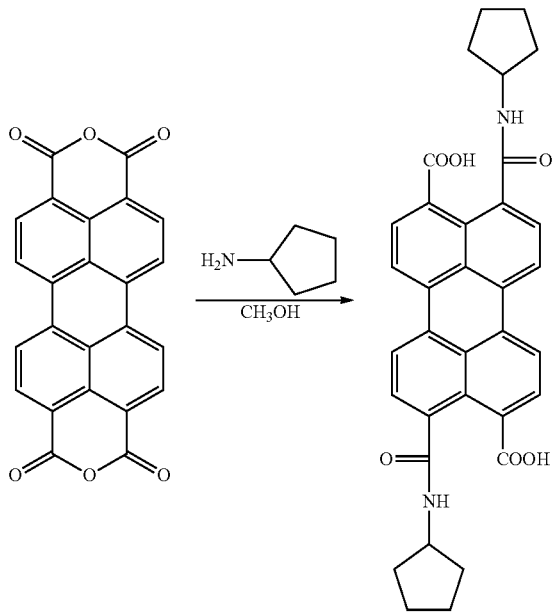

3,4,9,10-Perylene tetracarboxylic acid dianhydride (99 mg) was added to dimethylacetamide (2 ml) and sonicated for 5 minutes to form a cloudy dispersion. Cyclopentylamine (43 mg) in dimethylacetamide (1 ml) was added dropwise to the dispersion with continuous stirring to obtain a clear red solution. $^1$H NMR and IR spectra of the product were consistent with assigned structure.

Conversion of 3,9-Perylenedicarboxylic acid-4,10-bis[cyclopentylamino)-carbonyl] to N,N'-bis(cyclopentyl)perylene diimide in Solid State

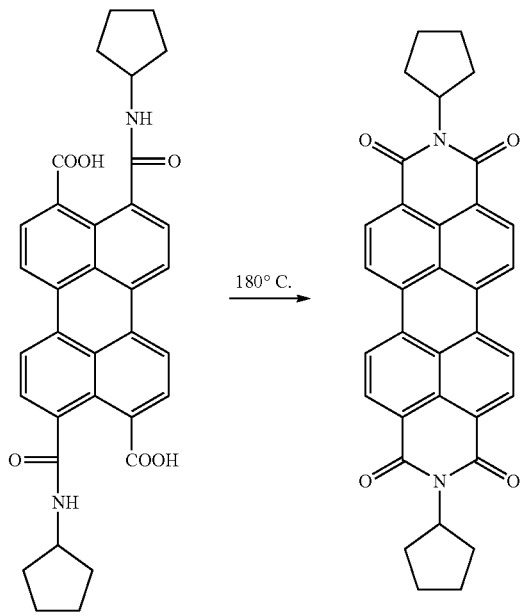

Figure 7A:
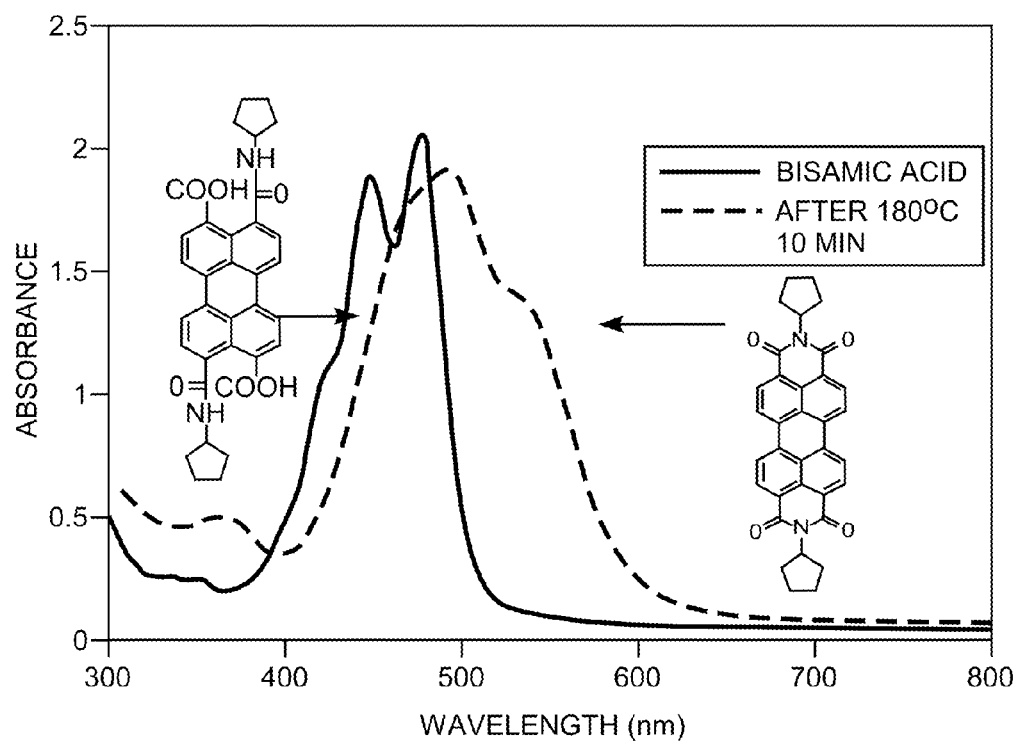
FIGS. 7A and 7B are graphical plots that provide data in Invention Example 7 below.
Figure 7B:
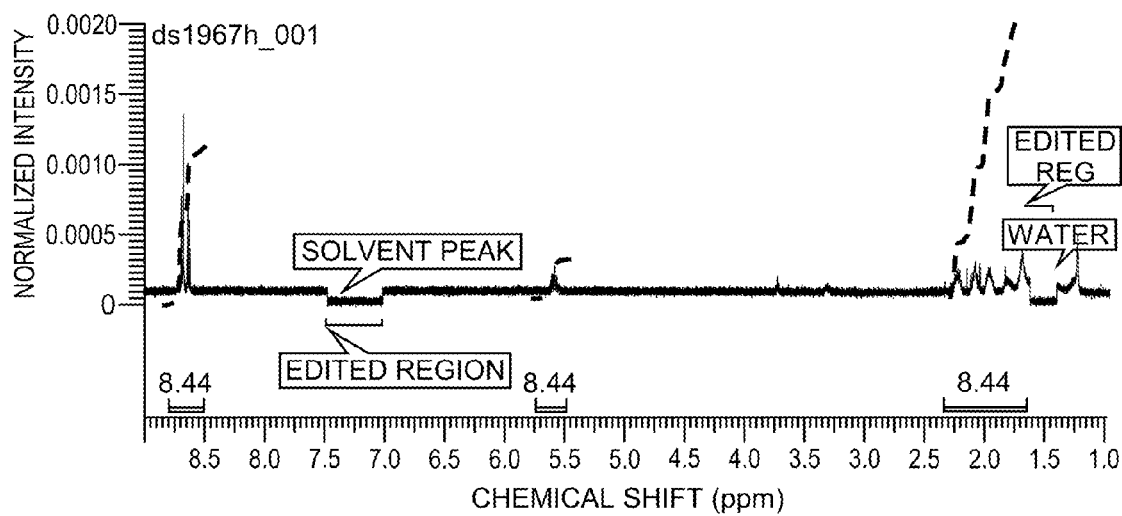

A solution of 3,9-perylenedicarboxylic acid-4,10-bis[cyclopentyl-amino)carbonyl] in methanol was drop cast onto a glass plate and heated to 180° C. for 10 minutes to form a coated article. Absorption spectrum of the thin film before after heating clearly showed the transformation of the coated amic acid to the corresponding arylene diimide compound with the manifestation of characteristic absorption bands of diimide (see FIG. 7A). The arylene diimide formed on the glass plate was extracted with CDCl$_3$ and the $^1$H NMR spectrum that was obtained was consistent with the assigned structure (see FIG. 7B). This spectrum was noisy due to poor solubility of the final product. This example shows the successful conversion of the amic acid of this invention to form a thin film semiconductor layer in a semiconducting article.

The invention has been described in detail with particular reference to certain preferred embodiments thereof, but it will be understood that variations and modifications can be effected within the spirit and scope of the invention.

PARTS LIST

10 substrate
20 gate dielectric
30 semiconductor
40 source electrode
50 drain electrode
60 gate electrode

The invention claimed is:

1. An organic composition that comprises an amic acid or amic ester, and includes one or more hydroxylic solvents that is methanol, ethanol, or a propanol in which the amic acid or amic ester is soluble or dispersible, wherein the amic acid or amic ester is an arylene tetracarboxylic acid or ester precursor that is represented by the following Structure (I) or (II):

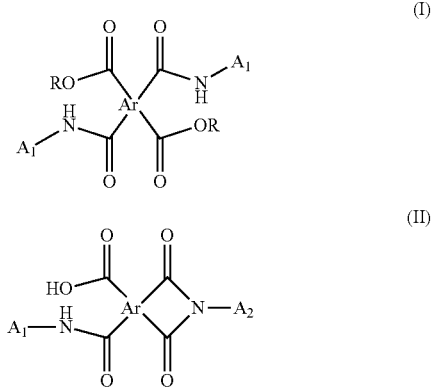

wherein Ar is an anthracene, naphthalene, or perylene nucleus and the four carbonyl groups are attached directly to peri carbon atoms, $A_1$ and $A_2$ are independently aryl, heteroaryl, non-aromatic alkyl, alkylaryl, fluoroalkyl, cycloalkyl, or heterocyclyl groups, and R is hydrogen or an alkyl or cycloalkyl group that is the same or different as that defined for $A_1$ and $A_2$.

2. The composition of claim 1 wherein the amic acid or amic ester is an arylene tetracarboxylic acid or ester precursor that is represented by the Structure (I) wherein Ar is naphthalene or perylene, $Ar_1$ is an alkyl, fluoroalkyl, alkylphenyl, phenyl, or cycloalkyl group, and R is hydrogen or a methyl or ethyl group.

3. The composition of claim 1 wherein the amic acid or amic ester is an arylene tetracarboxylic acid or ester precursor that is represented by the Structure (II) wherein Ar is naphthalene or perylene, and $A_1$ and $A_2$ are independently alkyl, fluoroalkyl, alkylphenyl, phenyl, or cycloalkyl groups, and R is hydrogen or a methyl or ethyl group.

4. The composition of claim 1 wherein the amic acid or amic ester is present in an amount of at least 0.5 and up to and including 10 weight % based on total composition weight.

5. The composition of claim 1 that consists essentially of the amic acid or amic ester.

6. The composition of claim 1 wherein the amic acid or amic ester is a precursor for an arylenetetracarboxylic acid or ester that is one of compounds I-1 through I-50:

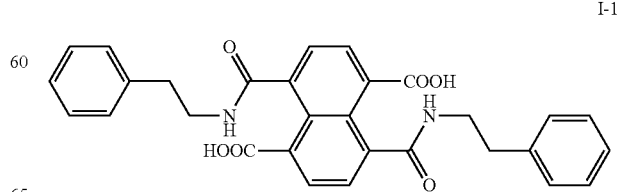

-continued
I-2
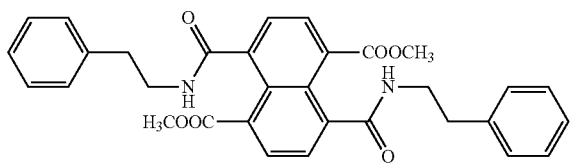
I-3
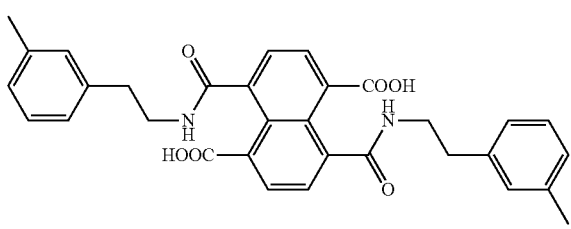
I-4
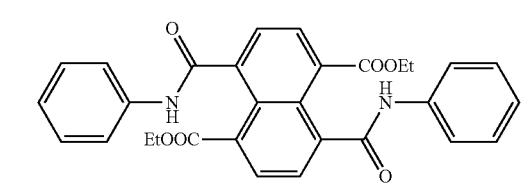
I-5
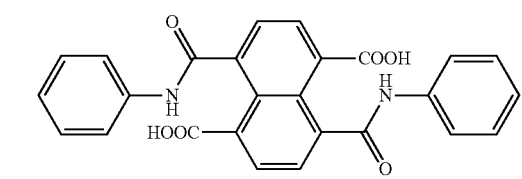
I-6
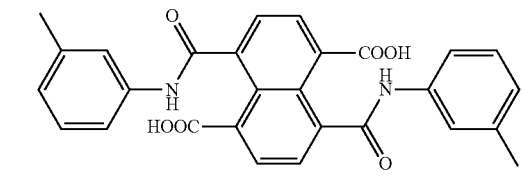
I-7
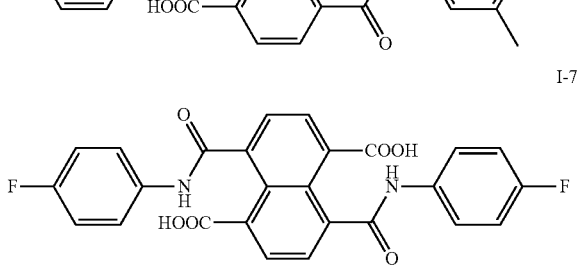
I-8
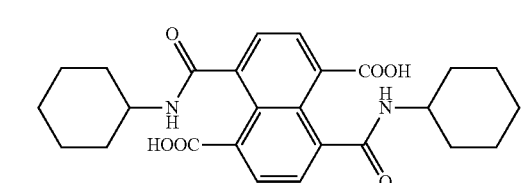
I-9
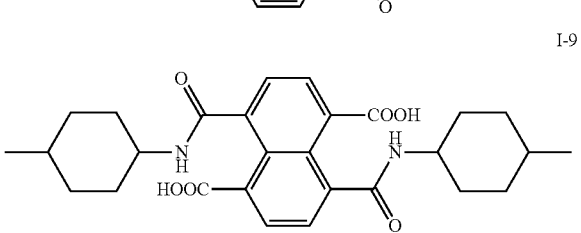
-continued
I-10
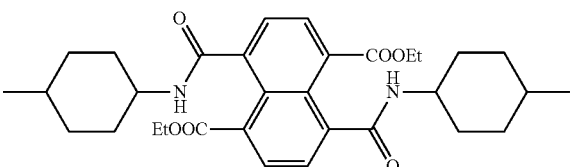
I-11
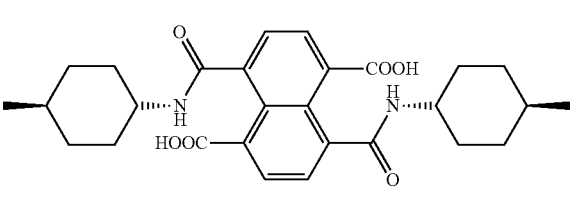
I-12
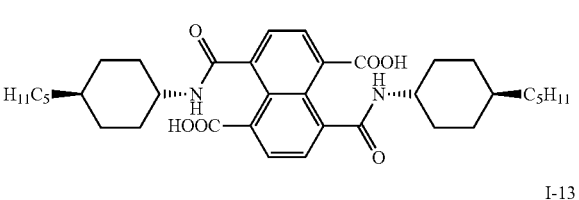
I-13
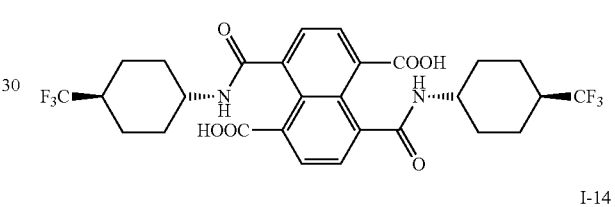
I-14
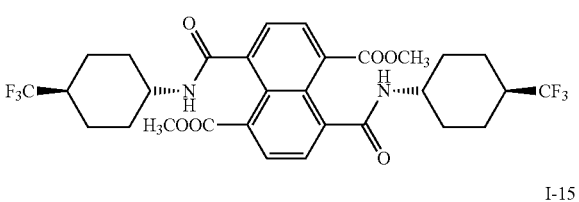
I-15
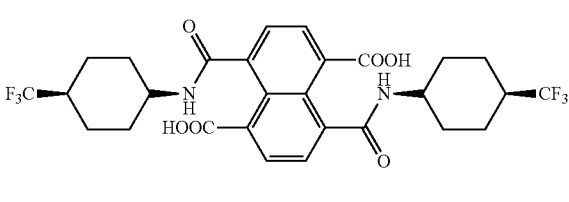
I-16
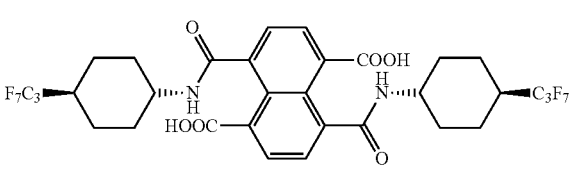
I-17
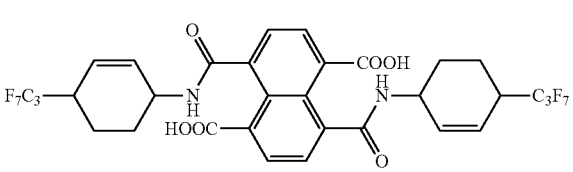

I-18
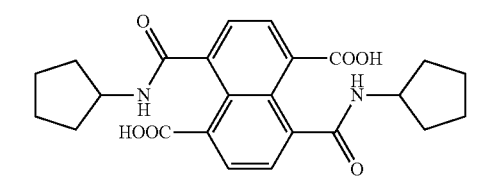
I-19
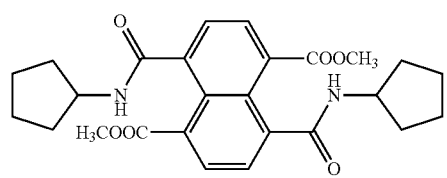
I-20
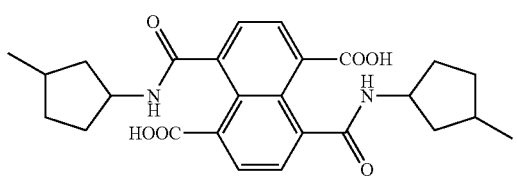
I-21
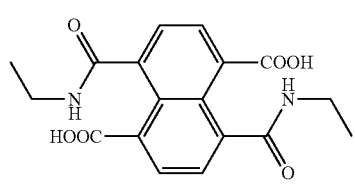
I-22
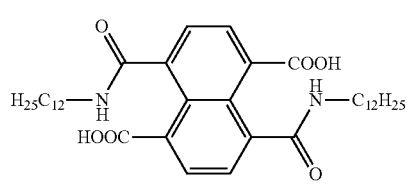
I-23
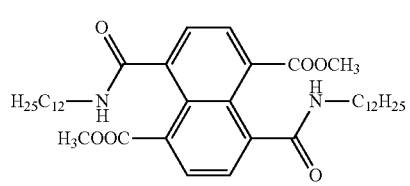
I-24
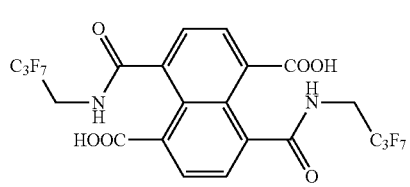
I-25
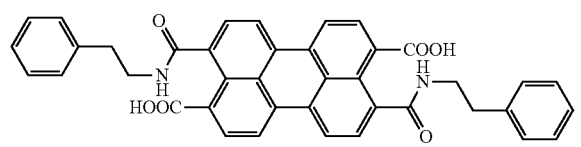
I-26
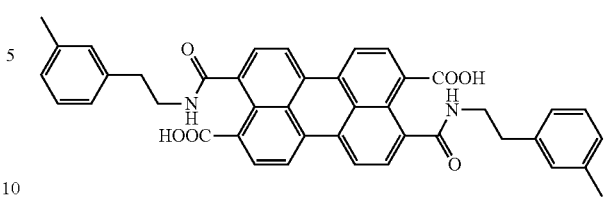
I-27
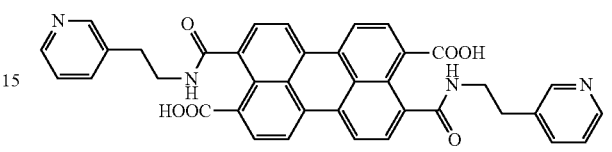
I-28
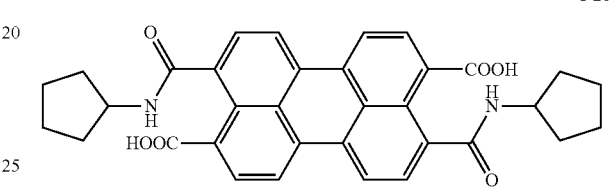
I-29
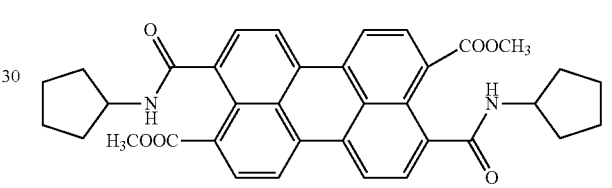
I-30
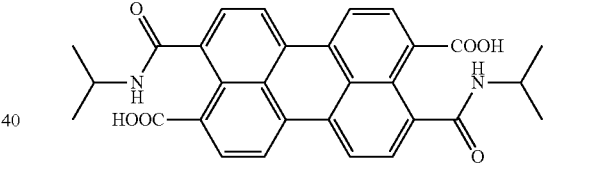
I-31
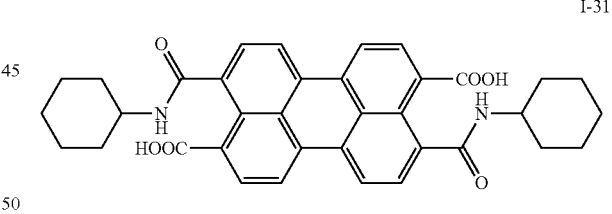
I-32
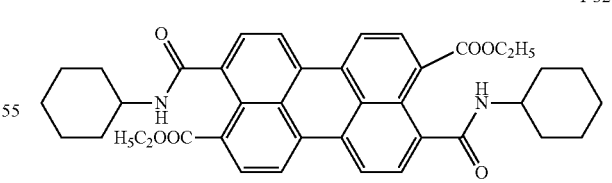
I-33
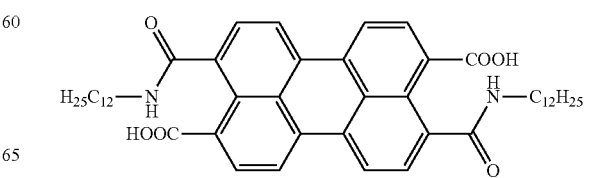

I-34
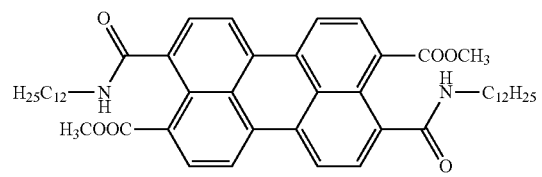
I-35
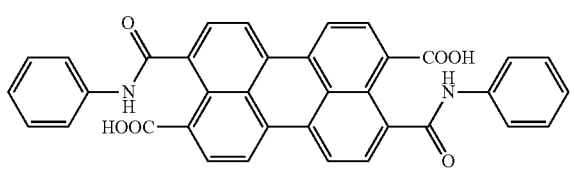
I-36
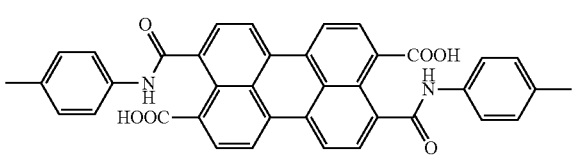
I-37
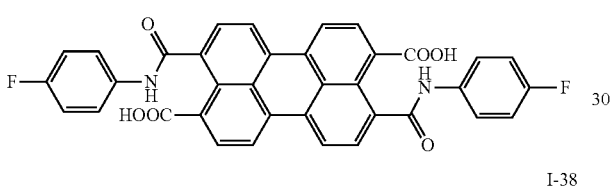
I-38
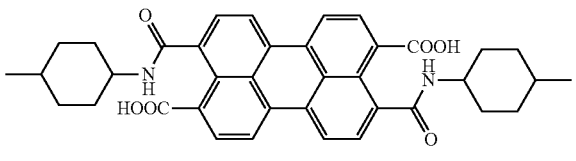
I-39
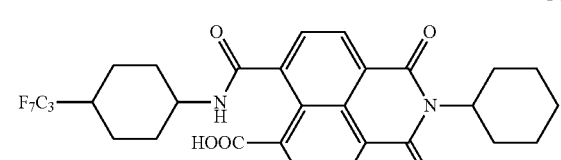
I-40
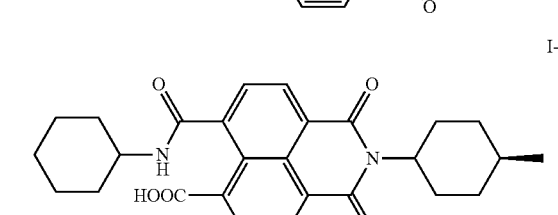
I-41
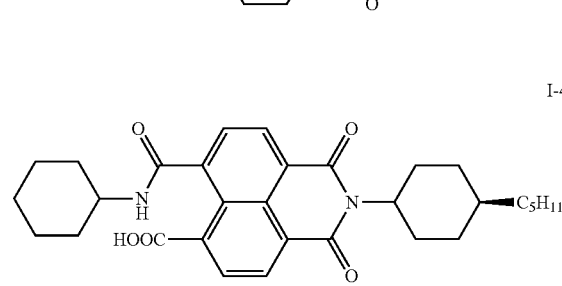
I-42
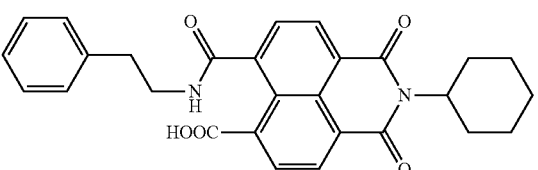
I-43
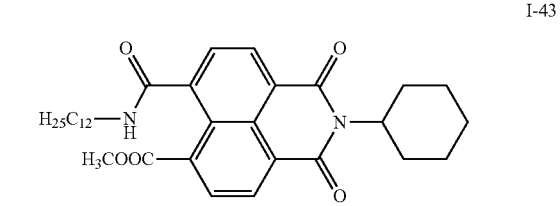
I-44
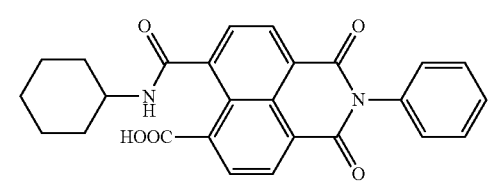
I-45
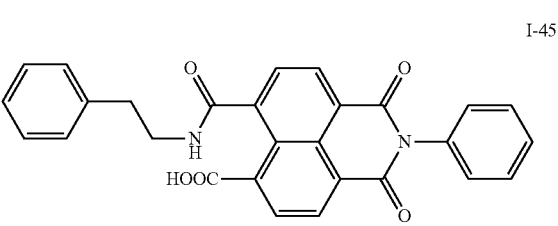
I-46
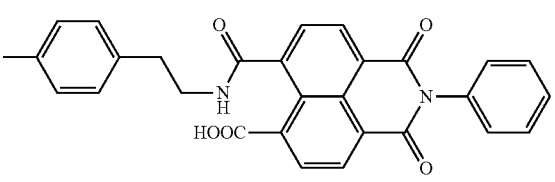
I-47
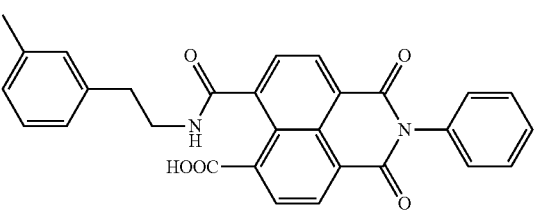

I-48

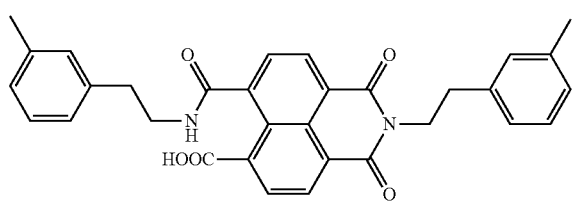

I-49

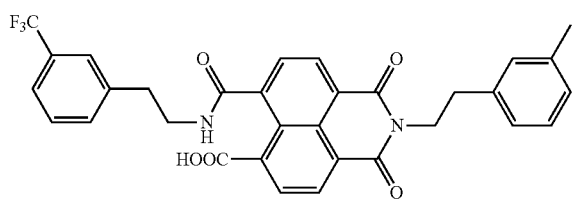

I-50

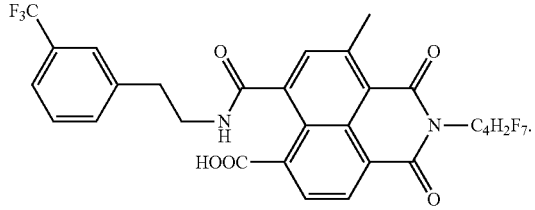

7. The organic composition of claim 1, wherein the amic acid or amic ester present in an amount of from 1 weight % to 50 weight %.

8. The organic composition of claim 1, comprising an alcohol as the hydroxylic solvent that is methanol, ethanol, or a propanol, and a mixture of an amic acid and an amic ester, each of which is an arylene tetracarboxylic acid or ester precursor that is represented by Structure (I) or Structure (II).

* * * * *